United States Patent [19]

Warrellow et al.

[11] Patent Number: 5,866,593
[45] Date of Patent: Feb. 2, 1999

[54] TRISUBSTITUTED PHENYL DERIVATIVES AND PROCESSES FOR THEIR PREPARATION

[75] Inventors: Graham John Warrellow, Northwood; Ewan Campbell Boyd, Tullibody; Rikki Peter Alexander, High Wycombe, all of United Kingdom

[73] Assignee: Celltech Therapeutics Ltd., Slough, United Kingdom

[21] Appl. No.: 964,041

[22] Filed: Nov. 4, 1997

Related U.S. Application Data

[63] Continuation of Ser. No. 361,421, Dec. 21, 1994, abandoned.

[30] Foreign Application Priority Data

Dec. 22, 1993 [GB] United Kingdom .............. 9326179
Jun. 23, 1994 [GB] United Kingdom .............. 9412598

[51] Int. Cl.[6] .......................... A61K 31/44; A61K 31/42; C07D 213/24; C07D 401/06
[52] U.S. Cl. .......................... 514/336; 514/340; 514/341; 514/342; 514/343; 514/277; 514/227.8; 514/255; 514/235.5; 514/318; 546/339; 546/193; 544/58.6; 544/360; 544/124
[58] Field of Search .................... 514/336, 340, 514/341, 342, 343, 277, 227.5, 255, 235.5, 318; 546/339, 193; 544/58.6, 360, 124

[56] References Cited

U.S. PATENT DOCUMENTS

| | | | |
|---|---|---|---|
| 4,012,495 | 3/1977 | Schmiechen et al. | 514/424 |
| 4,015,017 | 3/1977 | Gazave | 514/687 |
| 4,153,713 | 5/1979 | Huth et al. | 514/423 |
| 4,193,926 | 3/1980 | Schmiechen et al. | 548/517 |
| 4,303,649 | 12/1981 | Jones | 514/8 |
| 4,788,195 | 11/1988 | Torley et al. | 514/252 |
| 4,792,561 | 12/1988 | Walker et al. | 514/312 |
| 4,876,252 | 10/1989 | Torley et al. | 514/224.8 |
| 4,897,396 | 1/1990 | Hubele | 514/275 |
| 4,921,862 | 5/1990 | Walker et al. | 514/312 |
| 4,966,622 | 10/1990 | Rempfler et al. | 71/92 |
| 4,971,959 | 11/1990 | Hawkins | 514/150 |
| 5,124,455 | 6/1992 | Lombardo | 546/181 |
| 5,128,358 | 7/1992 | Sccomano et al. | 514/392 |
| 5,159,078 | 10/1992 | Rempfler et al. | 544/330 |
| 5,175,167 | 12/1992 | Zipperer et al. | 514/277 |
| 5,177,085 | 1/1993 | Naef | 514/307 |
| 5,236,918 | 8/1993 | Amschler et al. | 514/247 |
| 5,274,002 | 12/1993 | Hawkins | 514/530 |
| 5,298,511 | 3/1994 | Waterson | 514/311 |
| 5,326,898 | 7/1994 | Chandraratna | 560/17 |
| 5,340,827 | 8/1994 | Beeley et al. | 514/352 |
| 5,491,147 | 2/1996 | Boyd et al. | 514/247 |
| 5,521,184 | 5/1996 | Zimmermann | 514/252 |
| 5,550,137 | 8/1996 | Beeley et al. | 514/354 |
| 5,580,888 | 12/1996 | Warrellow | 514/332 |
| 5,593,997 | 1/1997 | Dow et al. | 514/258 |
| 5,608,070 | 3/1997 | Alexander et al. | 546/270 |
| 5,622,977 | 4/1997 | Warrellow | 514/336 |

(List continued on next page.)

FOREIGN PATENT DOCUMENTS

| | | |
|---|---|---|
| 0 233 461 A2 | 8/1987 | European Pat. Off. . |
| 0 295 210 A1 | 12/1988 | European Pat. Off. . |
| 0 337 943 A2 | 10/1989 | European Pat. Off. . |
| 0 393 500 A1 | 10/1990 | European Pat. Off. . |
| 0 490 823 A1 | 6/1991 | European Pat. Off. . |
| 0 470 805 A1 | 2/1992 | European Pat. Off. . |
| 0 497 564 A1 | 8/1992 | European Pat. Off. . |
| 0 511 865 A1 | 11/1992 | European Pat. Off. . |

(List continued on next page.)

OTHER PUBLICATIONS

Dent, Br. J. Pharmacol., vol. 103, pp. 1339–1346, 1991.

Ashton, "Selective Type IV Phosphodiesterase Inhibitors as Antiasthmatic Agents. The Syntheses and Biological Activities of 3–(Cyclopentyloxy)–4–methyoxybenzamides and Analogues", J. Med. Chem., 1994, 37, 1696–1703.

Beavo & Reifsnyder, "Primary Sequence of Cyclic Nucleotide Phosphodiesterase Isozymes and the Design of Selective Inhibitors" *TIPS*, 1990, 11, 150–155.

Buu–Hoi, N.P. et al., "Bromination of some 1,2,2–Triarylethylenes" J. of Organic Chemistry, 1958, 1261–1263.

(List continued on next page.)

*Primary Examiner*—John Kight
*Assistant Examiner*—D. Margaret M. Mach
*Attorney, Agent, or Firm*—Woodcock Washburn Kurtz Mackiewicz & Norris LLP

[57] ABSTRACT

Compounds of the general formula (1)

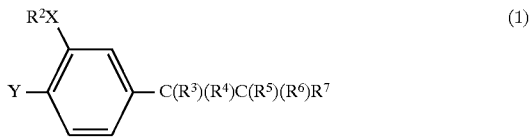

are described wherein Y is halogen or —OR$^1$, where R$^1$ is optionally substituted alkyl; X is —O—, —S— or —N(R$^8$)-, where R$^8$ is hydrogen or alkyl; R$^2$ is optionally substituted alkyl, alkenyl, cycloalkyl or cycloalkenyl; R$^3$ is hydrogen, halogen or —OR$^9$, where R$^9$ is hydrogen or optionally substituted alkyl, alkenyl, alkoxyalkyl, or alkanoyl, or formyl, carboxamido or thiocarboxamido; R$^4$ is —(CH$_2$)$_n$Ar, where Ar is monocyclic or bicyclic aryl optionally containing one or more heteroatoms selected from oxygen, sulfur and nitrogen atoms, wherein Ar is substituted by an optionally substituted C$_{3-9}$cycloaliphatic group optionally containing one or more heteroatoms selected from oxygen, sulphur or —N(R$^8$)-, and n is zero or an integer 1, 2 or 3; R$^5$ is —(CH$_2$)$_n$Ar' where Ar' is monocyclic or bicyclic aryl optionally containing one or more heteroatoms selected from oxygen, sulfur or nitrogen atoms or is Ar; R$^6$ is hydrogen or optionally substituted alkyl; and R$^7$ is hydrogen or optionally substituted alkyl; or a salt, solvate or hydrate thereof. Compounds according to the invention are potent and selective phosphodiesterase type IV inhibitors and are useful in the prophylaxis and treatment of diseases such as asthma where an unwanted inflammatory response or muscular spasm is present.

24 Claims, No Drawings

U.S. PATENT DOCUMENTS

| | | | |
|---|---|---|---|
| 5,693,659 | 12/1997 | Head et al. | 514/357 |
| 5,723,460 | 3/1998 | Warrellow et al. | 514/247 |
| 5,739,144 | 4/1998 | Warrellow et al. | 514/277 |

FOREIGN PATENT DOCUMENTS

| | | |
|---|---|---|
| 0 537 742 A2 | 4/1993 | European Pat. Off. . |
| 0 564 409 A1 | 10/1993 | European Pat. Off. . |
| 250 1443 | 7/1975 | Germany . |
| 3-77872 | 4/1991 | Japan . |
| 3-77923 | 4/1991 | Japan . |
| 2545 356 A1 | 11/1984 | Puerto Rico . |
| 1588639 | 4/1981 | United Kingdom . |
| WO 87/06576 | 11/1987 | WIPO . |
| WO 91/15451 | 10/1991 | WIPO . |
| WO 91/16892 | 11/1991 | WIPO . |
| WO 92/00968 | 1/1992 | WIPO . |
| WO 92/06085 | 4/1992 | WIPO . |
| WO 92/06963 | 4/1992 | WIPO . |
| WO 92/07567 | 5/1992 | WIPO . |
| WO 92/12961 | 8/1992 | WIPO . |
| WO 92/19594 | 11/1992 | WIPO . |
| WO 92/19602 | 11/1992 | WIPO . |
| WO 93/10118 | 5/1993 | WIPO . |
| WO 93/19748 | 10/1993 | WIPO . |
| WO 94/02465 | 2/1994 | WIPO . |
| WO 94/10118 | 5/1994 | WIPO . |
| WO 94/12461 | 6/1994 | WIPO . |
| WO 94/13661 | 6/1994 | WIPO . |
| WO 94/14742 | 7/1994 | WIPO . |
| WO 94/20446 | 9/1994 | WIPO . |
| WO 94/20455 | 9/1994 | WIPO . |
| WO 95/09847 | 4/1995 | WIPO . |
| WO 95/09851 | 4/1995 | WIPO . |
| WO 95/09852 | 4/1995 | WIPO . |
| WO 95/09853 | 4/1995 | WIPO . |
| WO 95/17386 | 6/1995 | WIPO . |
| WO 95/31451 | 11/1995 | WIPO . |
| WO 95/33727 | 12/1995 | WIPO . |
| WO 95/35281 | 12/1995 | WIPO . |
| WO 95/35283 | 12/1995 | WIPO . |
| WO 96/14843 | 5/1996 | WIPO . |
| WO 97/09297 | 3/1997 | WIPO . |

OTHER PUBLICATIONS

Buu–Hoi et al., "New Method for the Synthesis of ω,ω–Diarylacetophenones Aminated in the Aromatic Nucleus. Plynitration of Triarylethylenes", *Chem. Abstr.*, 1964, 61(13), 16006h.

Chan, A.C. et al., "The Role of Protein Tyrosine Kinases and Protein Tyrosine Phosphatases in T Cell Antigen Receptor Signal Transduction", Annu. Rev. Immunol., 1994, 12, 555–592.

Chemical Abstracts, "Hypoglycemic Pharmaceuticals Containing Manzammide Derivatives", Chem. Abstr., 1983, 99(6), No. 43558Z.

Chemical Abstracts. Registry Handbook—Number Section. Printed Issues Columbus US *compounds with registry No. 95992–21–5; 95971–60–1; 90053–37–5; 82668–18–6; 80395–25–1; 49610–49–3.

Daves, G.D. et al., "Pyrimidines, XIII. 2– and 6–Substituted 4–Pyrimidinecarboxylic Acids", *J. Of Hev. Chem.*, 1964, 1, 130–133.

Dietl, F. et al., "Chinone von Benzo–und Dibenzokronenethern", Synthesis, 1985, 626–631.

Dent et al., "Inhibition of eosinophil cyclic nucleotide PDE activity and opsonised zymosan–stimulated respiratory burst by 'type IV'–selective PDE inhibitors", Br. J. Pharmacol., 1991, 103, 1339–1346.

El–Wakil et al., "Study of the proton magnetic resonance of methoxytamoxifen towards ortho–substitiution", Chem. Abstr., 1992, 116, 255248t.

Geissler, J.F. et al., "Thiazolidine–Diones. Biochemical and Biological Activity of a Novel Class of Tyrosine Protein Kinase Inhibitors", J. Of Biol. Chem., 1990, 265(36), 22255–22261.

Grammaticakis, "Contribution A L'Etude de L'Absortion Dans L'Ultraviolet Moyen Et Le Visible Des N–Aroyl–Arylamines. IV. 2,3–, 3,4– et 2,4–, dimethoxybenzoylarylamines", *Bulletin DeLa Societa Chemique De France*, 1965, 848–858.

Green and Wuts, "Protective Group in Organic Synthesis", John Wiley & Sons, New York, 1991.

Hanks, S.K. et al., "The eukaryotic protein kinase superfamily: kinase (catalytic) domain structure and classification", *FASEB J.*, 1995, 9, 576–596.

Heaslip et al., "Phosphodiesterase–IV Inhibition, Respiratory Muscle Relaxation and Bronchodilation by WAY–PDA–641", *J. Pharm. Exper. Ther.*, 1993, 268(2), 888–896.

Hirose et al., "Styrene Derivatives and Electrophotpgraphic Photoreceptor Containing Them", *Chem. Abstr.*, 1993, 118, 136183z.

Ishikura, M. et al., "An Efficient Synthesis of 3–Heteroarylpyridines via Diethyl–(3–pyridyl)–borane" *Synthesis*, 1984, 936–938.

Iwashita, S. et al., "Signal Transduction System for Growth Factor Receptors Associated with Tyrosine Kinase Activity: Epidermal Growth Factor Receptor Singalling and Its Regulation", *Cellular Signalling*, 1992, 4(2), 123–132.

Karlsson et al., "T–Lymphocyte and Inflammatory Cell Research in Asthma", Joller, G. et al. (eds.), Academic Press, 1993, 323–347.

Lisle, H. et al., "IL–2–Induced Eosinophilia in the Rat Pleural Cavity: The Effect of Dexamethasone and Indomethacin", *Br. J. Pharmacol.* 1993, 108, 230.

Livi et al., "Cloning and Expression of cDNA for a Human Low-$K_m$3 Rolipram–sensitive Cyclic AMP Phosphodiesterase", Molecular and Cellular Biol. 1990, 10(6), 2678–2686.

Manhas et al., "heterocyclic Compounds XII. Quinazoline Derivatives as Potential Antifertility Agents(1)" *J. Heterocyclic Chem.*, 1979, 16, 711–715.

Mathison et al., "Synthesis and Hypotensive Properties of Tetrahydroixoquinolines", *J. Med. Chem.*, 1973, 16(4), 332–336.

Meyers, A.J. et al., "Oxazolines. XI. Synthesis of Functionalized Aromatic and Aliphatic Acids. A Useful Protecting Group for Carboxylic Acids Against Grignard and Hydride Reagents", *J. Org. Chem.* 1974, 39(18), 2787–2793.

Mezheritskaya, "Synthesis and properties of carboxonium het=erocyclic systems. VII. Synthesis and properties of 2–benzyl–substituted 1,3–dioxolanium salts", *Chem. Abstr.*, 1980, 93, 95160j, 635.

Mitsunobu, O., "The Use of Diethyl Azodicarboxylate and Triphenylphosphine in Synthesis and Transformation of Natural Products" *Synthesis,* 1981, 1–28.

Miyaura, N. et al., "The Palladium–Catalyzed Cross–Coupling Reaction of Phenylboronic Acid with Haloarenes in the Presence of Bases", *Synth. Comm.*, 1981, 11, 513–519.

Newton, A.C., "Protein Kinase C: Structure, Function, Regulation", *J. Biol. Chem.*, 1995, 270(48), 28495–28498.

Nicholson et al., "Differential Modulation of Tissue Function and Therapeutic Potential of Selective Inhibitors of Cyclic Nucleotide Phosphodiesterase Isoenzymes" *TIPS,* 1991, 12, 19–27.

O'Connor et al., "Voltammetry and Controlled Potential Oxidation of 3,4–dimethoxypropenylbenzene at a rotating platinum electrode in unbuffered acetonitrile and in acetonitrile–pyridine solution" *Chem. Abstr.*, 1964, 60(8) #10203.4.

Ohtani, Y. et al., "Studies on Pitch Problems Caused by Pulping and Bleaching of Tropical Woods. XIV. Chemistry of the Aurone Derivatives at the Conventional Bleaching Stages", *Acta Chem. Scand.*, 1982, 613–621.

Pines, J., "Cyclins and cyclin–dependent kinases: take your partners", *TIBS*, 1993, 18, 195–197.

Plé, N. et al., "Metalation of Diazines. XI. Directed Ortho–Lithiation of Fluoropyrimidines and Application to Synthesis of an Azacarboline", J. Heterocyclic Chem., 1994, 31, 1311–1315.

Porter et al., "Preparation of 6–phenyl–3–(5–tetrazolyl)pyridin–=2(H)–one Derivatives as Cyclic AMP–dependent Protein Kinase Agonists"Chem. Abstr., 1992, 117(9), 90296n.

Ramalingam, Deshmukh and Sattur, "Synthesis and Pharmacology of 2,5–Disubstituted 1,3,4–Zxadiazoles" *J. Indian Chem. Soc.*, 1981, 58(3), 269–271.

Reddy et al., "Inhibition of Breast Cancer Cell Growth in vitro by a Tyrosine Kinase Inhibitor" *Cancer Research*, 1992, 52, 3636–3641.

Sakakibara, K. et al., "Preparation of N–pyridyl–4–(benzuloxy) benzamides as Cardiotonics", *Chem. Abstr.*, 1988, 108, No. 131583p.

Sánchez, H.I. et al., "Formal Total Syntehsis of β–Pipitzol", *Tetrahedron*, 1985, 41(12), 2355–2359.

Schneider et al., "Catechol Estrogens of the 1,1, 2–Triphenylbut–1–ene Type: Relationship Between Structure, Estradiol Receptor Affinity, Estrogenic and Antiestrogenic Properties, and Mammary Tumor Inhibiting Activities" *J. Med. Chem.*, 1986, 29, 1355–1362.

Seitz et al., "Fluorotamoxifen. A Caveat on the Generality of Electrophilic Destannylation" *Chem. Abstr.*, 1989, 111, 57133k.

Sharp, M.J. et al., "Synthetic Connections to the Aromatic Directed Metalation Reaction. Functionalized Aryl Boronic Acids by Ipso Borodesilylation; General Synthesis of Unsymmetrical iphenyls and n–Terphenyls", Tetrahedron Lett., 1987, 28(43), 5093–5096.

Shioiri et al., "New Methods and Reagents in Organic Synthesis. 3. Diethyl Phosphorocyanidate: A New Reagent for C–Acylation", *J. Org. Chem.*, 1978, 43, 3631–3632.

Takeuchi, I. et al., "On the Antimocrobial Activity and Syntheses of Carbanilide and Salicylanilide Derivatives", *Chem. Abstr.*, 1983, 98, No. 125577y.

Thompson, W.J. and Gaudino, J., "A General Synthesis of 5–Arylnicotinates" *J. Org. Chem.*, 1984, 49, 5237–5243.

Tominaga et al., "Polarized Ethylenes. IV. Synthesis of Polarized Ethylenes Using Thioamides and Methyl Dithiocarboxylates and Their Application to Syntheses of Pyrazoles, Pyrimidines, Pyrazolo [3,4–d]pyrimidines, and 5–Aza [2.2.3]cyclazines", J. Het. Chem., 1990, 27, 647–660.

Trost and Fleming (eds.), *Comprehensive Organic Synthesis*, Pergamon Press, New York, 1991, 3, 531–541.

Tsutsumi, K. et al., "Preparation of (Dialkoxyphosphinoylmethyl) benzamides as Antihyperlipidemics", *Chem. Abstr.*, 1990, 113, No. 6599a.

Vidal et al., "Electrophilic Amination: Preparation and Use of N–Boc–3–(4–cyanophenyl)oxaziridine, A New Reagent That Transfers a N–Boc Group to N– and C–Nucleophiles", *J. Org. Chem.*, 1993, 58, 4791–4793.

Yeadon et al., "Mechanisms Contributing to Ozone–Induced Bronchial Hyperreactivity in Guinea Pigs", *Pulmonary Pharm.*, 1992, 5, 39–50.

Yoneda et al., "the Antiproliferative Effects of Tyrosine Kinase Inhibitors Tyrphostins on a Human Squamous Cell Carcinoma in Vitro and in Nude Mice" *Cancer Research*, 1991, 51, 4430–4435.

Kefalas, P. et al., "Signalling by the p60$^{c-src}$ Family of Protein–Tyrosine Kinases", *Int. J. Biochem. Cell Biol.*, 1995, 27(6), 551–563.

Chatterjee, A. et al., "Total Synthesis of Ring–C Aromatic 18–Nor Steroid", *Tetrahedron*, 1980, 36, 2513–2519.

Clayton, S.E. et al., "Direct Aromatic tert–Butylation during the Synthesis of Thoichroman–4–ones", Tetrahedron, 1993, 49(4), 939–946.

Collins, R.F. et al., "The Chemotherapy of Schistosomiasis. Part IV. Some Ethers of 4–Amino–2–methoxyphenol", *J. Chem. Soc.*, 1961, 1863–1879.

Degani, I. et al., "Cationi etero–aromatici Nota VI—Sintesi di alcuni derivati del perclorato di tiacromilio", *Boll. Sci. Fac. Chim. Ind. Bologna*, 1966, 24(2–3), 75–91 (English Summary Only).

Geissler et al., "Biochemical and Biological Activity of a Novel Class of Tyrosine Protein Kinase Inhibitors", *J. Biol. Chem.*, 1990, 265(36), 22255–22261.

Griffin, R.W. et al., "1–Methyl–7–halo–2–naphthalenecarboxylic Acid Derivatives", J. Organic Chem., 1964, 29(8), 2109–2116.

Gupta, A.S. et al., "Friedel–Crafts Condensation of Ethyl Allylmalonate with Anisole", *Tetrahedron*, 1967, 23, 2481–2490.

Hart et al., "Alkylation of Phenol with a Homoallylic Halide", *J. Am. Chem. Soc.*, 1963, 85, 3269–3273.

Johnson et al., "Identification of Retinoic Acid Receptor β Subtype Specific Agonists", *J. Med. Chem.*, 1996, 39(26), 5027–5030.

Lehmann, J. et al., "Lactones; XIII. Grignard Reaction Followed by Phase–Transfer Oxidation: A Convenient Synthesis of γ,γ–Distributed γ–Butyrolactones from γ–Butyrolactone", *Synthesis*, 1987, 1064–1067 (English abstract only).

Meyers, A.I. et al., "The Synthesis of 2–Pyridones from Cyclic Cyano Ketones. A New Aromatization Procedure for Dihydro–2–pyridones",*J. Org. Chem.*, 1964, 29, 1435–1438.

Pickett, W.C. et al., "Modulation of Eicosanoid Biosynthesis by Novel Pyridinylpyrimidines",*Ann. N.Y. Acad. Sci.*, 1994, 744, 299–305.

Spada, A.P. et al., "Small Molecule Inhibitors of Tyrosine Kinase Activity", *Exp. Opin. Ther. Patents*, 1995, 5(8), 805–817.

Yamaguchi, H., "Guanidinobenzene derivatives as anticoagulants", *Chem. Absts.*, 1989, 110, 655 (Abstract No. 94706z).

Zimmerman, J. et al., "Phenylamino–Pyrimidine (PAP) Derivatives: A New Class of Potent and Selective Inhibitors of Protein Kinase C (PKC)", *Arch. Pharm.*, 1996, 329(7), 371–376.

Zimmerman, J. et al, "Phenylamino–Pyrimidine (PAP)—Derivatives: A New Class of Potent and Highly Selective PDGF–Receptor Autophosphorylation Inhibitors", *Bioorg. Med. Chem. Lett.*, 1996, 6(11), 1221–1226.

Zimmerman, J. et al., "Potent and Selective Inhibitors of the ABL–Kinase Phenylamino–Pyrimidine (PAP) Derivatives", *Bioorg. Med. Chem. Lett.*, 1997, 7(2), 187–192.

TRISUBSTITUTED PHENYL DERIVATIVES AND PROCESSES FOR THEIR PREPARATION

This is a continuation of application Ser. No. 08/361,421, filed Dec. 21, 1994 now abandoned.

This invention relates to a novel series of tri-substituted phenyl derivatives, to processes for their preparation, to pharmaceutical compositions containing them, and to their use in medicine.

Many hormones and neurotransmitters modulate tissue function by elevating intra-cellular levels of adenosine 3', 5'-cyclic monophosphate (cAMP). The cellular levels of cAMP are regulated by mechanisms which control synthesis and breakdown. The synthesis of cAMP is controlled by adenyl cyclase which may be directly activated by agents such as forskolin or indirectly activated by the binding of specific agonists to cell surface receptors which are coupled to adenyl cyclase. The breakdown of cAMP is controlled by a family of phosphodiesterase (PDE) isoenzymes, which also control the breakdown of guanosine 3', 5'-cyclic monophosphate (cGMP). To date, seven members of the family have been described (PDE I–VII) the distribution of which varies from tissue to tissue. This suggests that specific inhibitors of PDE isoenzymes could achieve differential elevation of cAMP in different tissues, [for reviews of PDE distribution, structure, function and regulation, see Beavo & Reifsnyder (1990) TIPS, 11: 150–155 and Nicholson et al (1991) TIPS, 12: 19–27].

There is clear evidence that elevation of cAMP in inflammatory leukocytes leads to inhibition of their activation. Furthermore, elevation of cAMP in airway smooth muscle has a spasmolytic effect. In these tissues, PDE IV plays a major role in the hydrolysis of cAMP. It can be expected, therefore, that selective inhibitors of PDE IV would have therapeutic effects in inflammatory diseases such as asthma, by achieving both anti-inflammatory and bronchodilator effects.

The design of PDE IV inhibitors has met with limited success to date, in that many of the potential PDE IV inhibitors which have been synthesised have lacked potency and/or have been capable of inhibiting more than one type of PDE isoenzyme in a non-selective manner. Lack of a selective action has been a particular problem given the widespread role of cAMP in vivo and what is needed are potent selective PDE IV inhibitors with an inhibitory action against PDE IV and little or no action against other PDE isoenzymes.

We have now found a novel series of tri-substituted phenyl derivatives, members of which compared to known structurally similar compounds are potent inhibitors of PDE IV at concentrations at which they have little or no inhibitory action on other PDE isoenzymes. These compounds inhibit the human recombinant PDE IV enzyme and also elevate cAMP in isolated leukocytes. The compounds of the invention are therefore of use in medicine, especially in the prophylaxis and treatment of asthma.

Thus according to one aspect of the invention, we provide a compound of formula (1)

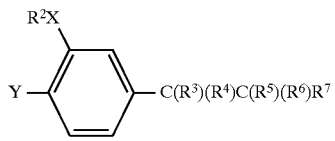

(1)

wherein
Y is a halogen atom or a group —OR$^1$ where R$^1$ is an optionally substituted alkyl group;

X is —O—, —S— or —N(R$^8$)-, where R$^8$ is a hydrogen atom or an alkyl group;

R$^2$ is an optionally substituted alkyl, alkenyl, cycloalkyl or cycloalkenyl group;

R$^3$ is a hydrogen or halogen atom or an —OR$^9$ group, where R$^9$ is a hydrogen atom or an optionally substituted alkyl, alkenyl, alkoxyalkyl, or alkanoyl group, or a formyl, carboxamido or thiocarboxamido group;

R$^4$ is a group —(CH$_2$)$_n$Ar where Ar is a monocyclic or bicyclic aryl group optionally containing one or more heteroatoms selected from oxygen, sulphur and nitrogen atoms, said Ar group being substituted by an optionally substituted C$_{3-9}$cycloaliphatic group optionally containing one or more heteroatoms selected from oxygen or sulphur atoms or —N(R$^8$)- groups, and n is zero or an integer 1, 2 or 3;

R$^5$ is a group —(CH$_2$)$_n$Ar', where Ar' is a monocyclic or bicyclic aryl group optionally containing one or more heteroatoms selected from oxygen, sulphur or nitrogen atoms or is an Ar group;

R$^6$ is a hydrogen atom or an optionally substituted alkyl group;

R$^7$ is a hydrogen atom or an optionally substituted alkyl group; and the salts, solvates, hydrates and N-oxides thereof.

It will be appreciated that the compounds of formula (1) may have one or more chiral centres, depending on the nature of the groups R$^3$, R$^5$, R$^6$ and R$^7$. Where one or more chiral centres is present, enantiomers or diastereomers may exist, and the invention is to be understood to extend to all such enantiomers, diastereomers and mixtures thereof, including racemates.

In the compounds of formula (1), when Y is a halogen atom it may be for example a fluorine, chlorine, bromine or iodine atom.

When Y in the compounds of formula (1) is a group —OR$^1$, R$^1$ may be, for example, an optionally substituted straight or branched alkyl group, for example, an optionally substituted C$_{1-6}$alkyl group, such as a methyl, ethyl, n-propyl or i-propyl group. Optional substituents which may be present on R$^1$ groups include one or more halogen atoms, e.g. fluorine, or chlorine atoms. Particular substituted alkyl groups include for example —CH$_2$F, —CH$_2$Cl, —CHF$_2$, —CHCl$_2$, —CF$_3$ or —CCl$_3$ groups.

Alkyl groups represented by R$^2$, R$^6$ or R$^7$ in the compounds of formula (1) include optionally substituted straight or branched C$_{1-6}$ alkyl groups, e.g. C$_{1-3}$ alkyl groups such as methyl or ethyl groups. Optional substituents on these groups include one, two or three substituents selected from halogen atoms, e.g. fluorine, chlorine, bromine or iodine atoms, or hydroxyl or C$_{1-6}$ alkoxy e.g. C$_{1-3}$ alkoxy such as methoxy or ethoxy groups.

Alkenyl groups represented by R$^2$ in the compounds of formula (1) include optionally substituted straight or branched C$_{2-6}$alkenyl groups such as ethenyl, propen-1-yl and 2-methylpropen-1-yl. Optional substituents include those described above in relation to the groups R$^2$, R$^6$ and R$^7$.

When R$^2$ in the compounds of formula (1) is an optionally substituted cycloalkyl or cycloalkenyl group it may be for example a C$_{3-8}$cycloalkyl group such as a cyclobutyl, cyclopentyl or cyclohexyl group or a C$_{3-8}$ cycloalkenyl group containing for example one or two double bonds such as a 2-cyclobuten-1-yl, 2-cyclopenten-1-yl, 3-cyclopenten-1-yl, 2,4-cyclopentadien-1-yl, 2-cyclohexen-1-yl, 3-cyclohexen-1-yl, 2,4-cyclohexadien-1-yl or 3,5-cyclohexadien-1-yl group, each cycloalkyl or cycloalkenyl group being optionally substituted by one, two or three substituents selected from halogen atoms, e.g. fluorine, chlorine, bromine or iodine atoms, straight or branched $C_{1-6}$alkyl e.g. $C_{1-3}$alkyl such as methyl or ethyl, hydroxyl or $C_{1-6}$alkoxy e.g. $C_{1-3}$alkoxy such as methoxy or ethoxy groups.

Alkyl groups represented by $R^8$ in compounds of formula (1) include straight or branched $C_{1-6}$ alkyl groups, e.g. $C_{1-3}$ alkyl groups such as methyl or ethyl groups. Thus for example when X in compounds of formula (1) is a —N($R^8$)- group it may be a —N(CH$_3$)- or —N(CH$_2$CH$_3$)- group. Alternatively, X may be a —NH— group.

When the group $R^3$ in compounds of formula (1) is a halogen atom it may be for example a fluorine, chlorine, bromine or iodine atom.

When the group $R^3$ in compounds of formula (1) is an —O$R^9$ group it may be for example a hydroxyl group; or a group —O$R^9$ where $R^9$ is an optionally substituted straight or branched $C_{1-6}$alkyl group, e.g. a $C_{1-3}$alkyl group such as a methyl or ethyl group, a $C_{2-6}$alkenyl group such as an ethenyl or 2-propen-1-yl group, a $C_{1-3}$alkoxy$C_{1-3}$alkyl group such as a methoxymethyl, ethoxymethyl or ethoxyethyl group, a $C_{1-6}$alkanoyl, e.g. $C_{1-3}$alkanoyl such as acetyl group, or a formyl [HC(O)—] or a carboxamido (CON$R^{11}R^{12}$) or thiocarboxamido (CSN$R^{11}R^{12}$) group, where $R^{11}$ and $R^{12}$ in each instance may be the same or different and is each a hydrogen atom or an optionally substituted straight or branched $C_{1-6}$alkyl, e.g. $C_{1-3}$alkyl group such as a methyl or ethyl group. Optional substituents which may be present on such $R^9$ groups include those described above in relation to the alkyl groups $R^2$, $R^6$ and $R^7$.

The cycloaliphatic substituent on the group Ar in $R^4$ or $R^5$ in compounds of formula (1) may be an optionally substituted $C_{3-9}$cycloaliphatic, e.g. a $C_{3-9}$cycloalkyl or $C_{3-9}$cycloalkenyl group, such as a $C_{4-7}$cycloalkyl or $C_{4-7}$cycloalkenyl group, optionally containing 1, 2, 3 or more heteroatoms selected from oxygen or sulphur atoms or —N($R^8$)- groups. Particular —N($R^8$)- groups include —NH— or —N(CH$_3$)- groups.

Particular examples of such cycloaliphatic groups include cyclobutyl, cyclopentyl, cyclohexyl, 2-cyclobuten-1-yl, 2-cyclopenten-1-yl, 3-cyclopenten-1-yl, 2,4-cyclopentadien-1-yl, 3,5-cyclohexadien-1-yl, pyrroline, e.g. 2- or 3- pyrrolinyl, pyrrolidinyl, dioxolanyl, e.g. 1,3-dioxolanyl, imidazolinyl, e.g. 2-imidazolinyl, oxazolinyl e.g. 2-oxazolinyl, imidazolidinyl, 2-oxazolidinyl, pyrazolinyl, e.g. 2-pyrazolinyl, pyrazolidinyl, pyranyl, e.g. 2- or 4-pyranyl, piperidinyl, 1,4-dioxanyl, morpholinyl, 1,4-dithianyl, thiomorpholinyl, piperazinyl, 1,3,5-trithianyl, oxazinyl, e.g. 2H-1,3-, 6H-1,3-, 6H-1,2-, 1,4-, 2H-1,2- or 4H-1,4-oxazinyl, isoxazinyl, e.g. -o- or p-isoxazinyl, oxathiazinyl, e.g. 1,2,5-, or 1,2,6- oxathiazinyl, or oxadiazinyl, e.g. 1,4,2-oxadiazinyl or 1,3,5,2-oxadiazinyl.

Optional substituents which may be present on such groups include those substituents discussed above in relation to the group $R^2$ when it is an alkyl group.

It will be appreciated that the cycloaliphatic substituent may be attached to the group Ar through either a ring carbon atom or heteroatom in the cycloaliphatic group and in the group Ar. Thus for example when the Ar group is a phenyl group the cycloaliphatic group may be attached through any carbon or heteroatom to any available carbon atom in Ar, particularly to the carbon atom at the 4-position relative to the Ar carbon atom attached to the remainder of the compound of formula (1).

In the compounds of formula (1) the group $R^4$ may be a group —Ar, —CH$_2$Ar, —(CH$_2$)$_2$Ar, —(CH$_2$)$_3$Ar. The group $R^5$ may be an —Ar', —CH$_2$Ar', —(CH$_2$)$_2$Ar', —(CH$_2$)$_3$Ar' or Ar group.

Monocyclic or bicyclic aryl groups represented by the group Ar or Ar' in compounds of formula (1) include for example $C_{6-12}$ optionally substituted aryl groups, for example optionally substituted phenyl, 1-or 2-naphthyl, indenyl or isoindenyl groups.

When the monocyclic or bicyclic aryl group Ar or Ar' contains one or more heteroatoms it may be for example a $C_{1-9}$ optionally substituted heteroaryl group containing for example one, two, three or four heteroatoms selected from oxygen, sulphur or nitrogen atoms. In general, Ar or Ar' heteroaryl groups may be for example monocyclic or bicyclic heteroaryl groups. Monocyclic heteroaryl groups include for example five- or six-membered heteroaryl groups containing one, two, three or four heteroatoms selected from oxygen, sulphur or nitrogen atoms.

Examples of heteroaryl groups represented by Ar or Ar' include pyrrolyl, furyl, thienyl, imidazolyl, N-methylimidazolyl, N-ethylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, pyrimidinyl, pyridazinyl, pyrazinyl, 1,3,5-triazinyl, 1,2,4-triazinyl, 1,2,3-triazinyl, benzofuryl, isobenzofuryl, benzothienyl, isobenzothienyl, indolyl, isoindolyl, benzimidazolyl, benzothiazolyl, benzoxazolyl, quinazolinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl and 5,6,7,8-tetrahydroisoquinolinyl.

The heteroaryl group represented by Ar or Ar' may be attached to the remainder of the molecule of formula (1) through any ring carbon or heteroatom as appropriate. Thus, for example, when the group Ar is a pyridyl group it may be a 2-pyridyl, 3-pyridyl or 4-pyridyl group. When it is a thienyl group it may be a 2-thienyl or 3-thienyl group, and, similarly, when it is a furyl group it may be a 2-furyl or 3-furyl group.

When in compounds of formula (1) the Ar or Ar' group is a nitrogen-containing heterocycle it may be possible to form quaternary salts, for example N-alkyl quaternary salts and the invention is to be understood to extend to such salts. Thus for example when the group Ar is a pyridyl group, pyridinium salts may be formed, for example N-alkylpyridinium salts such as N-methylpyridinium.

The aryl or heteroaryl groups Ar' represented by $R^5$ in compounds of formula (1) may optionally be substituted by one, two, three or more substituents [$R^{10}$]. The substituent $R^{10}$ may be selected from an atom or group $R^{13}$ or —Alk$^1$($R^{13}$)$_m$ wherein $R^{13}$ is a halogen atom, or an amino (—NH$_2$), substituted amino, nitro, cyano, hydroxyl (—OH), substituted hydroxyl, cycloalkoxy, formyl [HC(O)—], carboxyl (—CO$_2$H), esterified carboxyl, thiol (—SH), substituted thiol, —C(O)Alk$^1$, —SO$_3$H, —SO$_2$Alk$^1$, —SO$_2$NH$_2$, —SO$_2$NHAlk$^1$, —SO$_2$N[Alk$^1$]$_2$, —CONH$_2$, —CONHAlk$^1$, CON[Alk$^1$]$_2$, —NHSO$_2$H, —NHSO$_2$Alk$^1$, —N[SO$_2$Alk$^1$]$_2$, —NHSO$_2$NH$_2$, —NHSO$_2$NHAlk$^1$, —NHSO$_2$N[Alk$^1$]$_2$, —NHC(O)Alk$^1$, or —NHC(O)OAlk$^1$ group; Alk$^1$ is a straight or branched $C_{1-6}$alkylene, $C_{2-6}$alkenylene, or $C_{2-6}$alkynylene chain optionally interrupted by one, two, or three —O—, or —S— atoms or —S(O)p-, [where p is an integer 1 or 2] or —N($R^8$)- groups; and m is zero or an integer 1, 2 or 3.

When in the group —Alk$^1$($R^{13}$)$_m$ m is an integer 1, 2 or 3, it is to be understood that the substituent or substituents $R^{13}$ may be present on any suitable carbon atom in —Alk$^1$. Where more than one $R^{13}$ substitutent is present these may be the same or different and may be present on the same or different carbon atom in Alk$^1$. Clearly, when m is zero and no substituent $R^{13}$ is present or when $Alk^1$ forms part of a group such as —$SO_2Alk^1$ the alkylene, alkenylene or alkynylene chain represented by $Alk^1$ becomes an alkyl, alkenyl or alkynyl group.

When $R^{13}$ is a substituted amino group it may be a group —$NH[Alk^1(R^{13a})_m]$ [where $Alk^1$ and m are as defined above and $R^{13a}$ is as defined above for $R^{13}$ but is not a substituted amino, a substituted hydroxyl or a substituted thiol group] or a group —$N[Alk^1(R^{13a})_m]_2$ wherein each —$Alk^1(R^{13a})_m$ group is the same or different.

When $R^{13}$ is a halogen atom it may be for example a fluorine, chlorine, bromine, or iodine atom.

When $R^{13}$ is a cycloalkoxy group it may be for example a $C_{5-7}$cycloalkoxy group such as a cyclopentyloxy or cyclohexyloxy group.

When $R^{13}$ is a substituted hydroxyl or substituted thiol group it may be a group —$OAlk^1(R^{13a})_m$ or —$SAlk^1(R^{13a})_m$ respectively, where $Alk^1$, $R^{13a}$ and m are as just defined.

Esterified carboxyl groups represented by the group $R^{13}$ include groups of formula —$CO_2Alk^2$ wherein $Alk^2$ is a straight or branched, optionally substituted $C_{1-8}$alkyl group such as a methyl, ethyl, n-propyl, i-propyl, n-butyl, i-butyl, s-butyl or t-butyl group; a $C_{6-12}$aryl$C_{1-8}$alkyl group such as an optionally substituted benzyl, phenylethyl, phenylpropyl, 1-naphthylmethyl or 2-naphthylmethyl group; a $C_{6-12}$aryl group such as an optionally substituted phenyl, 1-naphthyl or 2-naphthyl group; a $C_{6-12}$aryloxy$C_{1-8}$alkyl group such as an optionally substituted phenyloxymethyl, phenyloxyethyl, 1-naphthyloxymethyl, or 2-naphthyloxymethyl group; an optionally substituted $C_{1-8}$alkanoyloxy$C_{1-8}$alkyl group, such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyloxypropyl group. Optional substituents present on the $Alk^2$ group include $R^{10}$ substituents described above.

When $Alk^1$ is present in or as a substituent $R^{10}$ it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupred by one, two, or three —O— or —S—, atoms or —S(O)—, —S(O)$_2$- or —N($R^8$)- groups.

Particularly useful atoms or groups represented by $R^{10}$ include fluorine, chlorine, bromine or iodine atoms, or $C_{1-6}$alkyl, e.g. methyl or ethyl, $C_{1-6}$alkylamino, e.g. methylamino or ethylamino, $C_{1-6}$ hydroxyalkyl, e.g. hydroxymethyl or hydroxyethyl, $C_{1-6}$alkylthiol e.g. methylthiol or ethylthiol, $C_{1-6}$alkoxy, e.g. methoxy or ethoxy, $C_{5-7}$cycloalkoxy, e.g. cyclo-pentyloxy, halo$C_{1-6}$alkyl, e.g. trifluoromethyl, $C_{1-6}$alkylamino, e.g. methylamino or ethylamino, amino (—$NH_2$), amino$C_{1-6}$alkyl, e.g. aminomethyl or aminoethyl, $C_{1-6}$dialkylamino, e.g. dimethylamino or diethylamino, nitro, cyano, hydroxyl (—OH), formyl [HC(O)—], carboxyl (—$CO_2H$), —$CO_2Alk^2$ [where $Alk^2$ is as defined above], $C_{1-6}$ alkanoyl e.g. acetyl, thiol (—SH), thio$C_{1-6}$alkyl, e.g. thiomethyl or thioethyl, sulphonyl (—$SO_3H$), $C_{1-6}$alkylsulphonyl, e.g. methylsulphonyl, aminosulphonyl (—$SO_2NH_2$), $C_{1-6}$alkylaminosulphonyl, e.g. methylaminosulphonyl or ethylaminosulphonyl, $C_{1-6}$dialkylaminosulphonyl, e.g. di-methylaminosulphonyl or diethylaminosulphonyl, carboxamido (—$CONH_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, sulphonylamino (—$NHSO_2H$), $C_{1-6}$alkylsulphonylamino, e.g. methylsulphonylamino or ethylsulphonylamino, $C_{1-6}$dialkylsulphonylamino, e.g. dimethylsulphonylamino or diethylsuiphonylamino, aminosulphonylamino (—$NHSO_2NH_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, $C_{1-6}$alkanoylamino, e.g. acetylamino, $C_{1-6}$alkanoylamino $C_{1-6}$alkyl, e.g. acetylaminomethyl or $C_{1-6}$alkoxycarbonylamino, e.g. methoxycarbonylamino, ethoxycarbonylamino or t-butoxycarbonylamino groups.

Where desired, two $R^{10}$ substituents may be linked together to form a cyclic group such as a cyclic ether, e.g. a $C_{2-6}$alkylenedioxy group such as ethylenedioxy.

It will be appreciated that where two or more $R^{10}$ substituents are present, these need not necessarily be the same atoms and/or groups. The $R^{10}$ substituents may be present at any ring carbon atom away from that attached to the rest of the molecule of formula (1). Thus, for example, in phenyl groups represented by Ar any substituent may be present at the 2-, 3-, 4-, 5- or 6- positions relative to the ring carbon atom attached to the remainder of the molecule.

In the compounds of formula (1), when an ester group is present, for example a group —$CO_2Alk^2$ this may advantageously be a metabolically labile ester.

Where desired, the aryl or heteroaryl group represented by Ar in compounds of formula (1) may additionally carry one or two extra substituents. Such substituents may in general by $R^{10}$ substituents as described above. Particularly useful substituents include halogen atoms, e.g. chlorine or fluorine atoms, $C_{1-6}$alkyl, e.g. methyl, $C_{1-6}$alkoxy, e.g. methoxy, halo$C_{1-6}$alkyl, e.g. trifluoromethyl, hydroxyl, formyl or carboxyl groups.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isethionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

In the compounds of formula (1), the group Y is preferably an —$OR^1$ group, especially where $R^1$ is an optionally substituted ethyl group or, especially, an optionally substituted methyl group. Especially useful substitutents which may be present on $R^1$ groups include one, two or three fluorine or chlorine atoms.

The group X in compounds of formula (1) is preferably —O—.

A particularly useful group of compounds of formula (1) has the formula (2):

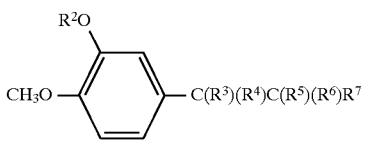

(2)

where $R^2$ is an optionally substituted cycloalkyl group; $R^3$, $R^4$, $R^5$, $R^6$ and $R^7$ are as defined for formula (1); and the salts, solvates, hydrates and N-oxides thereof.

In the compounds of formulae (1) or (2) $R^2$ is preferably an optionally substituted methyl or cyclopentyl group. In particular, $R^2$ is a cyclopentyl group.

The group $R^3$ in compounds of formulae (1) or (2) is preferably a hydroxyl group, or, especially, a hydrogen atom.

In compounds of formulae (1) or (2) the group $R^6$ is preferably a methyl group, or especially a hydrogen atom.

The group $R^7$ in compounds of formulae (1) or (2) is preferably a methyl group, or especially a hydrogen atom.

In one preference, $R^6$ and $R^7$ in compounds of formula (1) is each a methyl group. In another preference, one of $R^6$ or $R^7$ is a methyl group and the other is a hydrogen atom. In general, however, $R^6$ and $R^7$ is each especially a hydrogen atom.

The group $R^4$ in compounds of formulae (1) or (2) is preferably a —CH$_2$Ar, or, especially, an —Ar or group.

The group $R^5$ in compounds of formula (1) is preferably a —CH$_2$Ar' or, especially, an Ar' group.

Particularly useful $R^5$ groups in the compounds of formulae (1) or (2) include those in which $R^5$ is a group Ar' in which Ar' is a monocyclic aryl group optionally containing one or more heteroatoms selected from oxygen, sulphur, or, in particular, nitrogen atoms, and optionally substituted by one, two, three or more $R^{10}$ substituents. In these compounds, when the group represented by Ar' is a heteroaryl group it is preferably a nitrogen-containing monocyclic heteroaryl group, especially a five- or six-membered nitrogen-containing heteroaryl group. Thus, in one preferred example, $R^5$ may be a six-membered nitrogen-containing heteroaryl group, for example an optionally substituted pyridyl, pyridazinyl, pyrimidinyl or pyrazinyl group. Particular examples include optionally substituted 2-pyridyl, 3-pyridyl or, especially, 4-pyridyl, 3-pyridazinyl, 4-pyridazinyl, 5-pyridazinyl, 2-pyrimidinyl, 4-pyrimidinyl, 5-pyrimidinyl, 2-pyrazinyl or 3-pyrazinyl. Particular five-membered nitrogen-containing heteroaryl groups include optionally substituted imidazolyl, e.g. 5-imidazolyl groups. The monocyclic aryl group may be a phenyl group or a substituted phenyl group, and the monocyclic heteroaryl group containing an oxygen or sulphur atom may be an optionally substituted 2-furyl, 3-furyl, 2-thienyl or 3-thienyl group.

One particularly useful group of compounds of formulae (1) or (2) is that wherein $R^5$ is a pyridyl, particularly a 2-, 3- or, especially, 4-pyridyl group, or is a monosubstituted pyridyl, or preferably a disubstituted pyridyl group.

When in compounds of formulae (1) or (2) $R^5$ is a substituted pyridyl group it may be for example a mono-or disubstituted pyridyl group, such as a mono- or disubstituted 2-pyridyl, 3-pyridyl or especially 4-pyridyl group substituted by one or two atoms or groups $R^{10}$ as defined above, in particular one or two halogen atoms such as fluorine or chlorine atoms, or methyl, methoxy, hydroxyl or nitro groups. Particularly useful pyridyl groups of these types are 2- or 4-monosubstituted-3-pyridyl or 2,4-disubstituted-3-pyridyl groups or, especially 3-monosubstituted-4-pyridyl or 3,5-disubstituted-4-pyridyl, Particularly useful $R^4$ groups in compounds of formulae (1) or (2) include those groups where $R^4$ is an optionally substituted pyridyl, or especially, phenyl group said pyridyl or phenyl groups being substituted by a $C_{3-9}$ cycloaliphatic group containing one or more —O— or —S— atoms or —N($R^8$)- groups. In these latter compounds the cycloaliphatic group may be attached to the phenyl group through the phenyl carbon atom at position 2-, 3- or, especially 4-, relative to the phenyl carbon atom attached to the remainder of the compound of formulae (1) or (2).

In general in compounds of formula (1) or (2), the group $R^4$ is preferably a phenyl group substituted in the 2-, 3- or, especially, 4-position relative to the carbon atom attached to the remainder of the compound of formulae (1) or (2), by an optionally substituted $C_{3-7}$cycloalkyl or $C_{3-7}$cycloalkenyl group optionally containing 1, 2, 3 or more heteroatoms selected from oxygen or sulphur atoms of —N($R^8$)- groups. Particular examples of such cycloalkyl or cycloalkenyl groups include cyclobutyl, cyclopentyl, cyclohexyl, 2-cyclopenten-1-yl, pyrrolidinyl, dioxolanyl, imidazolinyl, oxazolinyl, pyranyl, piperidinyl, 1,4-dioxanyl, morpholinyl, thiomorpholinyl and piperazinyl groups. In a further group of compounds of this type, the phenyl group may additionally be substituted by one or two substituents $R^{10}$, particularly by one or two chlorine or fluorine atoms or methyl, methoxy, trifluoromethyl, hydroxyl, formyl or carboxyl groups.

A particularly useful group of compounds according to the invention has the formula (2) wherein $R^3$, $R^6$ and $R^7$ is each a hydrogen atom and $R^2$, $R^4$ and $R^5$ are as defined for formula (1); and the salts, solvates, hydrates and N-oxides thereof. Compounds of this type in which $R^2$ is a cycloalkyl or substituted cycloalkyl group, especially a substituted cyclopentyl or in particular a cyclopentyl group are particularly useful. In this group of compounds, $R^5$ is preferably a six-membered nitrogen-containing monocyclic heteroaryl group, especially a pyridyl or substituted pyridyl group in particular a 4-pyridyl or substituted 4-pyridyl group and $R^4$ is preferably an optionally substituted phenyl group substituted by a $C_{3-9}$ cycloaliphatic group containing one or more —O— or —S— atoms or —N($R^8$)- groups.

Particularly useful compounds according to the invention include:

(±)-4-{2-(3-Cyclopentyloxy-4-methoxyphenyl)-2-[4-(4,4-dimethyl-2-oxazolinyl)phenyl]-2-hydroxyethyl}pyridine; or (±)-4-{2-(3-Cyclopentyloxy-4-methoxyphenyl)-2-[4-(4,4-dimethyl-2-oxazolinyl)phenyl]ethyl}pyridine;

or the resolved enantiomers thereof;

and the salts, solvates, hydrates and N-oxides thereof.

Compounds according to the invention are selective and potent inhibitors of PDE IV. The ability of the compounds to act in this way may be simply determined by the tests described in the Examples hereinafter.

The compounds according to the invention are thus of particular use in the prophylaxis and treatment of human diseases where an unwanted inflammatory response or muscular spasm (for example bladder or alimentary smooth muscle spasm) is present and where the elevation of cAMP levels may be expected to prevent or alleviate the inflammation and relax muscle.

Particular uses to which the compounds of the invention may be put include the prophylaxis and treatment of asthma, especially inflamed lung associated with asthma, or in the treatment of inflammatory airway disease, chronic bronchitis, eosinophilic granuloma, psoriasis and other benign and malignant proliferative skin diseases, endotoxic shock, septic shock, ulcerative colitis, Crohn's disease, reperfusion injury of the myocardium and brain, inflammatory arthritis, chronic glomerulonephritis, atopic dermatitis, urticaria, adult respiratory distress syndrome, diabetes insipidus, allergic rhinitis, allergic conjunctivitis, vernal conjunctivitis, arterial restenosis and ortherosclerosis.

Compounds of the invention also suppress neurogenic inflammation through elevation of cAMP in sensory neurones. They are, therefore, analgesic, anti-tussive and anti-hyperalgesic in inflammatory diseases associated with irritation and pain.

Compounds according to the invention may also elevate cAMP in lymphocytes and thereby suppress unwanted lymphocyte activation in immune-based diseases such as rheumatoid arthritis, ankylosing spondylitis, transplant rejection and graft versus host disease.

Compounds according to the invention have also been found to reduce gastric acid secretion and therefore can be used to treat conditions associated with hypersecretion.

Compounds of the invention suppress cytokine synthesis by inflammatory cells in response to immune or infectious stimulation. They are, therefore, useful in the treatment of bacterial fungal or viral induced sepsis and septic shock in which cytokines such as tumour necrosis factor (TNF) are key mediators. Also compounds of the invention suppress inflammation and pyrexia due to cytokines and are, therefore, useful in the treatment of inflammation and cytokine-mediated chronic tissue degeneration which occurs in diseases such as rheumatoid or osteo-arthritis.

Over-production of cytokines such as TNF in bacterial, fungal or viral infections or in diseases such as cancer, leads to chachexia and muscle wasting. Compounds of the invention ameliorate these symptoms with a consequent enhancement of quality of life.

Compounds of the invention elevate cAMP in certain areas of the brain and thereby counteract depression and memory impairment.

Compounds of the invention suppress cell proliferation in certain tumour cells and can be used, therefore, to prevent tumour growth and invasion of normal tissues.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular inflammatory condition will vary depending on the compound chosen, and the condition of the patient to be treated. In general, however, daily dosages may range from around 100 ng/kg to 100 mg/kg, e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds according to the invention may be prepared by the following processes. The symbols Y, $R^2$, $R^3$, $R^4$, $R^5$, $R^6$, $R^7$ and X, when used in the formulae below are to be understood to represent those groups described above in relation to formula (1) unless otherwise indicated. In the reactions described below it may be necessary to protect reactive functional groups, for example hydroxy, amino, thio, or carboxy groups, where these are desired in the final product, to avoid their unwanted participation in the reactions. Conventional protecting groups may be used in accordance with standard practice [see, for example, Green, T. W. in "Protective Groups in Organic Synthesis" John Wiley and Sons, 1981.] It may be that deprotection will form the last step in the synthesis of compounds of formula (1).

Thus according to a further aspect of the invention, a compound of formula (1) wherein $R^3$ and $R^7$ is each a hydrogen atom may be prepared by hydrogenation of a compound of formula (3):

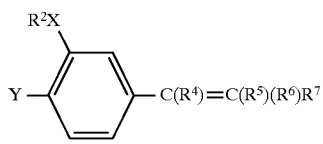

(3)

The hydrogenation may be performed using for example hydrogen in the presence of a catalyst. Suitable catalysts include metals such as platinum or palladium, optionally supported on an inert carrier such as carbon or calcium carbonate; nickel e.g. Raney nickel, or rhodium. The reaction may be performed in a suitable solvent, for example an alcohol such as methanol or ethanol, an ether such as tetrahydrofuran or dioxane or an ester such as ethyl acetate, optionally in the presence of a base, for example a tertiary organic base such as triethylamine, at for example ambient temperature.

Alternatively, the reaction may be accomplished by transfer hydrogenation using an organic hydrogen donor and a transfer agent. Suitable hydrogen donors include for example acids, such as formic acid, formates, e.g. ammonium formate, alcohols, such as benzyl alcohol or ethylene glycol, hydrazine, and cycloalkenes such as cyclohexene or cyclohexadiene. The transfer agent may be for example a transition metal, for example palladium or platinum, optionally supported on an inert carrier as discussed above, nickel e.g. Raney nickel, ruthenium, e.g. tris(triphenylphosphine) ruthenium chloride or copper. The reaction may generally be performed at an ambient or elevated temperature, optionally in the presence of a solvent, for example an alcohol such as ethanol or an acid such as acetic acid.

Intermediates of formula (3) may be prepared using a Horner-Wadsworth-Emmons approach by reaction of a ketone of formula (6) [described hereinafter] with a phosphonate $R^5CH_2PO(OAlk)_2$, where Alk is a $C_{1-4}$alkyl group such as a methyl group, in the presence of a base such as sodium hydride. The phosphonates for use in this reaction may be prepared by conventional methods, for example by reaction of a compound $R^5CH_2L$, where L is a leaving group such as a chlorine atom with a phosphine $P(OAlk)_3$.

In another process for the preparation of intermediates of formula (3), an alkene of formula (4):

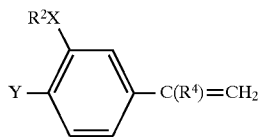

(4)

may be coupled in a Heck reaction with an organopalladium compound derived from a compound $R^5Hal$ [where Hal is a halogen atom such as a bromine atom] and a palladium salt such as palladium acetate in the presence of a phosphine such as tri-o-tolyl phosphine and a base such as triethylamine at an elevated temperature and pressure.

Intermediate alkenes of formula (4) may be obtained by reaction of a corresponding ketone of formula (6) [described hereinafter] using a Wittig reaction employing a phosphonium salt such as methyltriphenylphosphonium bromide in the presence of a base such as n-butyllithium and an inert solvent such as tetrahydrofuran at, for example, 0° C. to ambient temperature.

Intermediates of formula (3) may also be prepared by dehydration of an alcohol of formula (5):

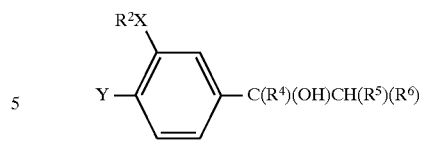

(5)

using an acid or base—catalysed elimination.

Suitable acids include for example phosphoric or sulphonic acids, e.g. 4-toluenesulphonic acid. The reaction may be performed in an inert organic solvent, for example a hydrocarbon such as toluene, at an elevated temperature, for example the reflux temperature. Base-catalysed elmination may be performed using for example trifluoroacetic anhydride in the presence of an organic base such as triethylamine at a low temperature e.g. from around 0° C. to ambient temperature, in a solvent such as dichloromethane or tetrahydrofuran.

In certain instances, the reaction conditions used may also cleave the group $R^2$ in the starting material of formula (4) to yield an intermediate of formula (3) where $R^2$ is a hydrogen atom. Such compounds may be converted to the required compound of formula (3) by reaction with a halide $R^2Hal$ (where Hal is a halogen atom such as a bromine or chlorine atom) as described hereinafter for the preparation of compounds of formula (1) from the corresponding compounds where $R^2$ is a hydrogen atom.

It will be appreciated that the alcohols of formula (5) are compounds of the invention in which the group $R^3$ is a hydroxyl group. Thus according to a further aspect of the invention, a compound of formula (1) wherein $R^3$ is a hydroxyl group and $R^7$ is a hydrogen atom may be prepared by reaction of a ketone of formula (6):

(6)

with an organometallic reagent $R^5R^6CHZ$, where Z is a metal atom.

Metal atoms represented by Z include, for example, a lithium atom.

The reaction may be performed in a solvent such as an ether, e.g. a cyclic ether such as tetrahydrofuran, at a low temperature e.g. around −70° C. to ambient temperature. This reaction is particularly suitable for the preparation of compounds of formula (1) wherein $R^5$ is an electron deficient group such as a 2- or 4-pyridyl group.

Reagents $R^5R^6CHZ$ are either known compounds or may be prepared, preferably in situ during the above process, by reaction of a compound $AlkCH_2Z$ [where Alk is an alkyl group such as a n-propyl group] with a compound $R^5R^6CH_2$ where necessary in the presence of a base such as an amine e.g. diisopropylamine using the above-mentioned conditions.

Ketones of formula (6) may be prepared by oxidation of a corresponding alcohol of formula (7):

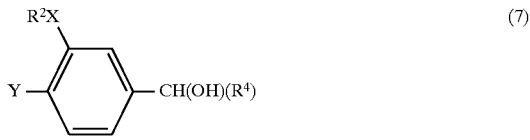

(7)

using an oxidising agent such as manganese dioxide in a solvent such as dichloromethane at ambient temperature.

Alternatively, ketones of formula (6) may be prepared by reaction of a halide of formula (8):

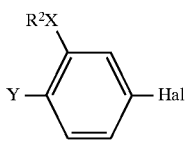

(8)

[where Hal is a halogen atom such as a bromine or chlorine atom] by halogen-metal exchange with a base such as n-butyllithium followed by reaction with a nitrile R⁴CN, an acid chloride R⁴COCl or an ester R⁴CO₂Alk (where Alk is an alkyl group, e.g. a methyl group), in a solvent such as tetrahydrofuran at a low temperature, e.g. around −70° C., and subsequent treatment with an acid such as hydrochloric acid at e.g. −20° C. to ambient temperature.

Alcohols of formula (7) may be prepared by reaction of an aldehyde of formula (9):

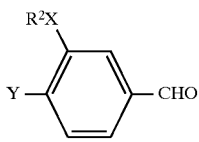

(9)

with an organometallic compound, such as an organolithium compound R⁴Li, or a Grignard reagent R⁴MgBr, in a solvent, such as tetrahydrofuran, at a low temperature, e.g. around −55° C. to 0° C.

Aldehydes of formula (9) may be prepared by alkylation of a corresponding compound of formula (10):

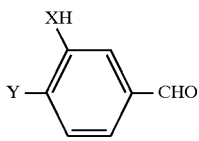

(10)

using a compound R²Hal [where Hal is as previously defined] using the reagents and conditions described hereinafter for the alkylation of intermediates of formula (18).

Intermediates of formula (10) are either known compounds or may be prepared from known starting materials by methods analogous to those used for the preparation of the known compounds.

Halides of formula (8) may be prepared by alkylation of a compound of formula (11):

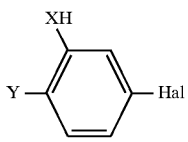

(11)

using the reagents and conditions discussed above in relation to the alkylation of aldehydes of formula (10).

Halides of formula (11) where X is —O— may be prepared by oxidation of an aldehyde of formula (12):

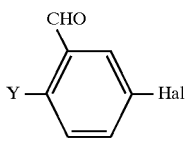

(12)

using an oxidising agent such as 3-chloroperoxybenzoic acid in a halogenated hydrocarbon such as chloroform at a temperature from around 0° C. to room temperature.

Aldehydes of formula (12) and halides of formula (11) where X is —S— or —N(R⁸)- are either known compounds or may be prepared from known starting materials by methods analogous to those used for the preparation of the known compounds.

In yet another process according to the invention, compounds of formula (1) wherein R³, R⁶ and R⁷ is each a hydrogen atom may be prepared by decarboxylation of an acid of formula (13):

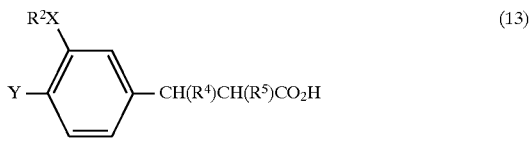

(13)

The reaction may be carried out by treatment of the compound of formula (13) with a base, for example an inorganic base such as a hydroxide, e.g. sodium hydroxide in a solvent such as an alcohol, e.g. ethanol, at an elevated temperature e.g. the reflux temperature, followed by acidification of the reaction mixture to a pH of around pH4 to around pH6 using an acid such as an inorganic acid, e.g. hydrochloric acid, at an elevated temperature, e.g. the reflux temperature.

If desired, the acid of formula (13) may be generated in situ from the corresponding ester or nitrile using the above reaction conditions, or by initial treatment with an acid.

Intermediates of formula (13) may be prepared by reacting a compound of formula (14)

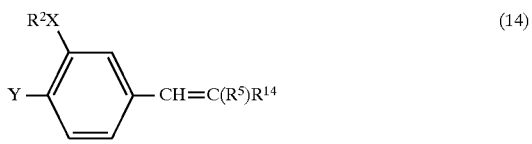

(14)

[where R¹⁴ is an ester of an acid —CO₂H (e.g. an alkyl ester such as an ethyl ester) or a group —CN], with a Grignard reagent R⁴MgBr, in the presence of a complexing agent, e.g. a copper (I) bromide-dimethyl sulphide complex, or a copper (1) chloride with an organolithium compound, e.g. R⁴Li, in a solvent, e.g. tetrahydrofuran, at low temperature, e.g. around −40° C., followed by treatment with a base or an acid to yield the acid of formula (13) where R¹⁴ is —CO₂H. The Grignard and the lithium reagents are either known compounds or may be prepared in a manner similar to that used to synthesise the known compounds.

Compounds of formula (14) may be obtained by reacting an adehyde of formula (9) with an ester or nitrile R⁵CH₂R¹⁴ in an acid solvent, such as acetic acid, at an elevated temperature, for example the reflux temperature, in the presence of a base, such as ammonium acetate.

In a further process according to the invention a compound of formula (1) wherein R³, R⁶ and R⁷ is each a hydrogen atom and R⁵ is a heteroaryl group may be generally prepared by cyclisation of a compound of formula (15):

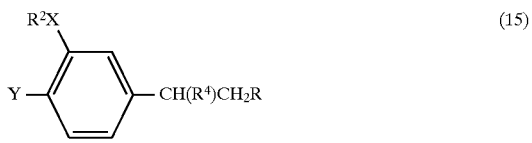

(15)

where R is a carboxylic acid [—CO₂H] group or a reactive derivative thereof; or a nitrile [—CN] or an imine salt with a bifunctional reagent W¹R⁵ᵃW² and, where necessary, a compound R⁵ᵇW³ [where W¹, W² and W³, which may be the same or different, is each a reactive functional group or a protected derivative thereof; and R⁵ᵃ and R⁵ᵇ are components of the heteroaryl group R⁵ such that when added together with $W^1$, $W^2$ and $W^3$ to the group R in compounds of formula (15) the resulting group —$RW^1R^{5a}W^2$ or —$RW^1R^{5a}W^2R^{5b}W^3$ constitutes the heteroaryl group $R^5$].

Reactive derivatives of carboxylic acids for use in this reaction include acid halides, (e.g. acid chlorides), amides, including thioamides, or esters, including thioesters. Imine salts include for example salts of formula [e.g.—C(OAlk)=$NH_2$+$A^-$, where Alk is a $C_{1-4}$alkyl group and $A^-$ is a counterion e.g. a chloride ion].

In this general reaction the reactive functional groups represented by $W^1$, $W^2$ or $W^3$ may be any suitable carbon, nitrogen, sulphur or oxygen nucleophiles. Particular examples include simple nucleophiles such as carbanions [e.g. generated by the coupling of an alkyl group with an organometallic compound], amino, thiol and hydroxyl groups.

In general, the cyclisation reaction will initially be performed in a solvent, for example an inert solvent such as a halocarbon, e.g. dichloromethane, an ether, e.g. a cyclic ether such as tetrahydrofuran, or a hydrocarbon, e.g. an aromatic hydrocarbon such as toluene, from a low temperature, e.g. around −70° C., to around the reflux temperature, where necessary in the presence of a base or a thiation reagent, e.g. Lawesson's reagent, followed if necessary by heating, to an elevated temperature, e.g. the reflux temperature.

Thus, in one particular example, compounds of formula (1) wherein $R^3$, $R^6$ and $R^7$ is each a hydrogen atom and $R^5$ is a benzothiazolyl, benzoxazolyl or benzimidazolyl group may be prepared by reaction of a compound of formula (15) where R is an acid halide, e.g. acid chloride, with a reagent $W^1R^{5a}W^2$ which is 2-aminothiophenol, 2-hydroxyphenol, or 1,2-diaminobenzene respectively in the presence of a base e.g. an organic amine such as pyridine, in a solvent e.g. a halocarbon such as dichloromethane, from around −70°C. to the reflux temperature.

In another example of the general cyclisation process, a compound of formula (15) where R is an acid halide as described above may be reacted with a compound $W^1R^{5a}W^2$ which is a monoalkylmalonate, e.g. ethyl hydrogen malonate, followed by reaction with a compound $R^{5b}W^3$ which is hydrazine to give a compound of formula (1) wherein $R^3$, $R^6$ and $R^7$ is each a hydrogen atom and $R^5$ is a 5-hydroxypyrazolyl group.

In another variation of the cyclisation process, the halide of formula (15) may be reacted with a compound $W^1R^{5a}W^2$ which is $BrMg(CH_2)_3$[—$O(CH_2)_2O$—] followed by reaction in an acid solution with a compound $R^{5b}W^3$ which is methylamine to yield a compound of formula (1) wherein $R^3$, $R^6$ and $R^7$ is each a hydrogen atom and $R^5$ is a N-methyl pyrrole group.

In a further example of the cyclisation process, the halide of formula (15) may be reacted with a compound $W^1R^{5a}W^2$ which is $H_2NNHCSNH_2$ in an aromatic hydrocarbon such as toluene, at an elevated temperature, e.g. around 150° C., followed by treatment with a base, e.g. an inorganic base such as sodium bicarbonate to give a compound of formula (1) wherein $R^3$, $R^6$ and $R^7$ is each a hydrogen atom and $R^5$ is a 1,2,4-triazolyl-5-thiolate group.

Intermediate compounds of formula (15) are particularly useful and form a further aspect of the invention. Active derivatives of the acids of formula (15) and other compounds of formula (15) where R is a nitrile or an imine salt may be prepared from the corresponding acids [where R is —$CO_2H$] using conventional procedures for converting carboxylic acids to such compounds, for example as described in the Examples hereinafter.

Acids of formula (15) [where R is —$CO_2H$] may be prepared by hydrolysing a diester of formula (16)

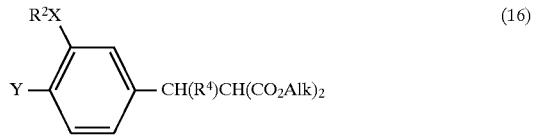

where Alk is a $C_{1-4}$alkyl group, e.g. an ethyl group, with a base, e.g. sodium hydroxide, in a solvent, e.g. dioxane, at an elevated temperature, e.g. the reflux temperature, followed by acidification at an elevated temperature.

Diesters of formula (16) may be prepared by reacting a diester of formula (17)

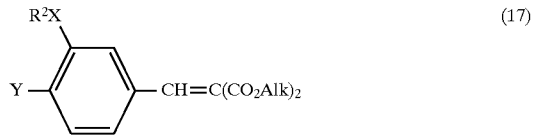

with an organometallic reagent, such as a Grignard reagent using the conditions described above for the preparation of alcohols of formula (1).

In another process according to the invention, a compound of formula (1) may be prepared by alkylation of a compound of formula (18):

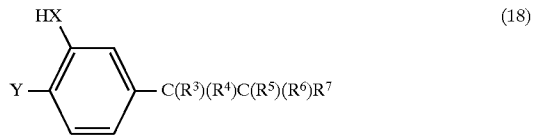

using a reagent $R^2L$, where L is a leaving group.

Leaving groups represented by L include halogen atoms such as iodine or chlorine or bromine atoms or sulphonyloxy groups such as arylsulphonyloxy groups, e.g. p-toluenesulphonyloxy.

The alkylation reaction may be carried out in the presence of a base, e.g. an inorganic base such as a carbonate, e.g. caesium or potassium carbonate, an alkoxide, e.g. potassium-t-butoxide, or a hydride, e.g. sodium hydride, in a dipolar aprotic solvent such as an amide, e.g. a substituted amide such as dimethylformamide or an ether, e.g. a cyclic ether such as tetrahydrofuran, at ambient temperature or above e.g. around 40° C. to 50° C.

Intermediates of formula (18) may be obtained from the corresponding protected compound of formula (19):

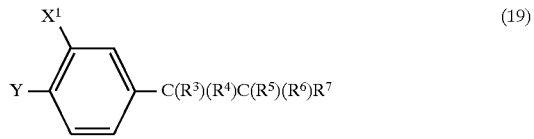

wherein $X^1$ is a protected hydroxy, thio or amino group using conventional procedures [see Green, T. W. ibid]. Thus, for example, where X is a t-butyldimethylsilyloxy group, the required hydroxyl group may be obtained by treatment of the protected intermediate with tetrabutylammonium fluoride. The protected intermediate of formula (18) may be prepared in an analogous manner to the compounds of formula (1) using the reactions described herein and appropriately protected intermediates.

Compounds of formula (17) may be prepared by condensing an aldehyde of formula (9) with a malonate, e.g. diethylmalonate, if necessary in the presence of catalysts, e.g. piperidine and acetic acid, in an inert solvent, e.g. toluene, at elevated temperature, e.g. the reflux temperature.

The cycloaliphatic substituent on the group Ar may be introduced at any stage during the synthesis of compounds of formula (1). For example, a compound of formula (1) wherein Ar is substituted by a 1,3-dioxolanyl, 1,3-dithiane, 1,3-dithiolane or 1,3-oxathiolane group may be prepared from the corresponding aldehyde or ketone by reaction with ethylene glycol or a group $HS(CH_2)_nSH$ or $HS(CH_2)_2OH$ using standard conditions.

Compounds of formula (1) may also be prepared by interconversion of other compounds of formula (1). Thus, for example, a group represented by $R^4$ or $R^5$ in compounds of formula (1) may be substituted in the aryl or heteroaryl portions by any of the groups $R^{10}$ by an appropriate substitution reaction using the corresponding unsubstituted compound of formula (1) and a $R^{10}$ containing nucleophile or electrophile.

In another example of an interconversion process a compound of formula (1) wherein the aryl or heteroaryl group in $R^4$ or $R^5$ contains a —$CH_2NH_2$ substituent may be prepared by reduction of a corresponding compound wherein $R^4$ or $R^5$ contains a nitrile group, using for example a complex metal hydride such as lithium aluminium hydride in a solvent such as an ether e.g. diethylether.

In a further example, a compound of formula (1) wherein the aryl or heteroaryl group in $R^4$ or $R^5$ contains an alkanoylamino or alkanoylaminoalkyl substituent may be prepared by acylation of a corresponding compound wherein $R^4$ or $R^5$ contains a —$NH_2$ or alkylamino group by reaction with an acyl halide in the presence of a base, such as a tertiary amine e.g. triethylamine in a solvent such as dichloromethane.

In yet another example of an interconversion process, compounds of formula (1) wherein $R^4$ or $R^5$ is substituted by an ester [$CO_2Alk^2$], e.g. an ethanoate, may be prepared by esterification of a corresponding compound wherein $R^4$ or $R^5$ contains a carboxylic acid, using an acid halide, such as an acid chloride, e.g. acetyl chloride, in an alcohol, such as ethanol, at an elevated temperature, such as the reflux temperature.

Compounds of formula (1) wherein $R^4$ or $R^5$ is substituted by a carboxylic acid may be prepared from the corresponding compound wherein $R^4$ or $R^5$ contains a formyl group, by oxidation with an oxidising agent, e.g. potassium permanganate, in a solvent, such as an alcohol, e.g. tert-butanol, at ambient temperature.

In a further interconversion reaction, compounds of formula (1) wherein $R^4$ or $R^5$ is substituted by an aminoalkyl group, such as dimethylaminomethyl, may be prepared by reductive amination of a corresponding compound wherein $R^4$ or $R^5$ contains a formyl group, using an amine, e.g. dimethylamine, in the presence of a reducing agent, e.g. sodium cyanborohydride, if necessary in the presence of a catalyst, e.g. ethanolic HCl, in a solvent, such as an alcohol, e.g. methanol, at ambient temperature.

In another example of an interconversion reaction a compound of formula (1) wherein $R^4$ or $R^5$ is substituted by a formyl group, may be reduced to the corresponding alcohol, e.g. where $R^4$ or $R^5$ contains a hydroxy-methyl group, using a reducing agent, e.g. sodium borohydride, in a solvent, such as an alcohol, e.g. ethanol, at a temperature from around 20° C. to ambient temperature. The resulting alcohol may then be converted to the corresponding alkoxy derivative, e.g. methoxymethyl, by reaction with an alkyl halide or alkyl sulphonate using the methods and reagents described above for the alkylation of intermediates of formula (18).

In a further example of an interconversion process compounds of formula (1) wherein $R^4$ or $R^5$ contains a carboxamido (—$CONHR^{11}$) or an aminocarbonyl (—$NHCOR^{11}$) group may be prepared by reaction of the corresponding compound wherein $R^4$ or $R^5$ contains a —$CO_2H$ or a —$NH_2$ group respectively by reaction with a carbamate, such as isobutyl chloroformate or ethyl chloroformate, in the presence of a base, such as an amine, e.g. triethylamine or N-methylmorpholine, in a solvent, such as dichloromethane, or a mixture of solventrs, e.g. tetrahydrofuran and dimethylformamide, at a temperature from around –20° C. to room temperature.

In a still further interconversion reaction, compounds of formula (1) wherein $R^4$ or $R^5$ is substituted by a —$NHCONHR^{11}$ group may be prepared by reacting a corresponding compound wherein $R^4$ or $R^5$ is substituted by an amino (—$NH_2$) group, with an isocyanate, e.g. ethyl isocyanate, in a solvent, e.g. dichloromethane, at ambient temperature.

In another example of an interconversion process, compounds of formula (1) wherein $R^7$ is an alkyl group, may be prepared by interconversion of a compound of formula (1) where $R^7$ is a hydrogen atom by reaction with a compound $R^7L$, where L is a leaving group, for example a halogen atom, such as chlorine, in the presence of a base, for example lithium diisopropylamide, in a solvent such as tetrahydrofuran, at low temperature, such as 0° C.

Compounds of formula (1) wherein $R^3$ is an $OR^9$ group where $R^9$ is an alkyl, alkoxyalkyl, formyl or alkanoyl group, may be prepared in another example of an interconversion process by reaction of a compound of formula (1) where $R^3$ is a —OH group with a compound $R^9L$ (where $R^9$ is as just defined and L is a leaving group as described above), in a solvent, such a dichloromethane or tetrahydrofuran in the presence of base, for example triethylamine or potassium tert-butoxide, at room temperature.

In a further interconversion process compounds of formula (1) wherein $R^9$ is a carboxamido (—$CONHR^{11}$) or a thiocarboxamido (—$CSNHR^{11}$) group, may be prepared by reaction of a compound of formula (1) wherein $R^3$ is a hydroxyl group with an isocyanate $R^{11}NCO$ or an isothiocyanate $R^{11}NCS$, in a solvent, for example chloroform, in the presence of a base, for example diisopropylethylamine, at ambient temperature. The isocyanate $R^{11}NCO$ and isothiocyanate $R^{11}NCS$ are known compounds or may be prepared in a conventional manner.

In a further example, a compound of formula (1) wherein $R^9$ is a $CONR^{11}R^{12}$ group may be prepared by reaction of a compound of formula (1) wherein $R^9$ is a $CONHR^{11}$ group with a reagent $R^{12}L$ (where L is a leaving group as described above) in the presence of a base, for example sodium hydride, in a solvent, such as tetrahydrofuran, at low temperature, for example 0° C.

In another example, an isothiocyanate of formula (1) where $R^9$ is —$CSNR^{11}R^{12}$ may be prepared by reacting a compound of formula (1) wherein $R^9$ is a (—$CONR^{11}R^{12}$) group with a thiation reagent, such as Lawesson's Reagent, in an anhydrous solvent, for example toluene, at elevated temperature, such as the reflux temperature.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate acid or base in a suitable solvent e.g. an organic solvent such as an ether, using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral acid or base. Suitable chiral acids include, for example, tartaric acid and other tartrates such as dibenzoyl tartrates and ditoluoyl tartrates, sulphonates such as camphor sulphonates, mandelic acid and other mandelates and phosphates such as 1,1'-binaphthalene-2,2'-diyl hydrogen phosphate. The diastereomers may then be separated by any convenient means, for example by crystallisation and the desired enantiomer recovered, e.g. by treatment with an acid or base in the instance where the diastereomer is a salt.

In another resolution process a racemate of formula (1) may be separated using chiral High Performance Liquid Chromatography. Alternatively, if desired a particular enantiomer may be obtained by using an appropriate chiral intermediate in one of the processes described above.

The following examples illustrate the invention. The following abbreviations are used: DMF—dimethylformamide; THF—tetrahydrofuran; DME—dimethoxyethane; EtOAc—ethyl acetate; $Et_2O$—diethylether; $Et_3N$—triethylamine; BuLi—butyllithium; LDA—lithium diisopropylamide; EtOH—ethanol; RT—room temperature.

All $^1$Hnmr spectra were obtained at 300 MHz unless specified otherwise.

INTERMEDIATE 1

3-Cyclopentyloxy-4-methoxybenzaldehyde $Cs_2CO_3$ (214 g, 0.66 mol) was added to a mixture of 3-hydroxy-4-methoxybenzaldehyde (100 g, 0.66 mol) and cyclopentyl bromide (98 g, 0.66 mol) in anhydrous DMF (500 ml). The reaction mixture was stirred at RT for 16 h then treated with a further portion of cyclopentyl bromide (98 g, 0.66 mol) and $Cs_2CO_3$ (214 g, 0.66 mol). After a further 6 h at RT, the mixture was filtered and concentrated in vacuo. The residue was dissolved in $CH_2Cl_2$ (300 ml) and washed with NaOH solution (10%; 2×150 ml). The organic layer was dried ($MgSO_4$), concentrated in vacuo, and distilled (150° C., $10^{-2}$ mbar) to afford the title compound (130 g) as a viscous colourless oil. $\delta_H$ (CDCl$_3$) 1.5–2.0 (8H, br m, C$\underline{H}_2$)$_4$), 3.87 (3H, s, OMe), 4.80 (1H, br m, OC$\underline{H}$CH$_2$), 6.90 (1H, d, J 8.7 Hz, Ar$\underline{H}$ ortho to OMe), 7.30–7.45 (2H, m, 2×Ar$\underline{H}$ meta to OMe), and 9.77 (1H, s, ArC$\underline{H}$O).

INTERMEDIATE 2

[4-(4,4-dimethyl-2-oxazolinyl)phenyl-3'-cyclopentyloxy-4'-methoxyphenyl)ketone

A solution of 2-(4-bromophenyl)-4,4-dimethyloxazoline (A. J. Meyers, D. L. Temple, D. Haidukewych and E. D. Milhelich J. Org. Chem, 39, 2787, 1974) (53.25 g, 0.21 mol) in THF (200 ml) was added dropwise to magnesium turnings (6.0 g, 0.25 g atoms). The reaction was stirred for 2 h at RT, then a solution of Intermediate 1 (46.0 g, 0.21 mol) in THF (200 ml) was added dropwise. The reaction was stirred for 16 h then heated to reflux for 1 h, cooled to RT and quenched with NH$_4$Cl solution (200 ml). The layers were separated and the aqueous layer extracted with EtOAc (2×250 ml). The organic layer was washed with brine (250 ml), dried (MgSO$_4$), then concentrated in vacuo to give an orange oil. The crude oil was dissolved in CH$_2$Cl$_2$ (350 ml) and treated with manganese dioxide (137 g, 1.58 mol) then stirred vigorously for 72 h. The mixture was filtered through Celite® and the residue washed with CH$_2$Cl$_2$ (300 ml). The filtrate was concentrated in vacuo and the residue triturated with Et$_2$O to give the title compound (59.4 g) as an off white amorphous powder m.p. 159° C. $\delta_H$ (CDCl$_3$) 1.41 (6H, s, CMe$_2$), 1.5–2.1 (8H, m, (C$\underline{H}_2$)$_4$), 3.92 (3H, s, OMe), 4.15 (2H, s, oxazoline C$\underline{H}_2$), 4.84 (1H, m, OC$\underline{H}$), 6.89 (1H, d, J 8.4 HZ, Ar$\underline{H}$ ortho to OMe), 7.35 (1H, dd, J 2.0, 8.4 Hz, Ar$\underline{H}$ para to OMe), 7.43 (1H, d, J 2.0 Hz, Ar$\underline{H}$ ortho to cyclopentyloxy), 7.78 (2H, d, J 8.5 Hz, ArH), and 8.03 (2H, d, J 8.5 Hz, ArH); $\nu_{max}$ (CDCl$_3$)1648 and 1271 cm$^{-1}$; m/z (ESI) 394 (M$^+$+1, 100%).

INTERMEDIATE 3

(E) and (Z) isomers of 4-{2-(3-Cyclopentyloxy-4-methoxyphenyl)-2-[4-(4,4-dimethyl-2-oxazolinyl)phenyl]ethenyl}pyridine Trifluoroacetic anhydride (2.47 g, 1.66 ml, 11.8 mmol) was added dropwise to a cooled (ice-bath) solution of the compound of Example 1 (4.75 g, 9.8 mmol) in CH$_2$Cl$_2$ (50 ml). The dark orange solution was treated dropwise with triethylamine (0.99 g, 1.36 ml, 11.8 mmol) and the reaction stirred for 16 h at RT then quenched with 10% Na$_2$CO$_3$ solution (25 ml). The mixture was extracted with CH$_2$Cl$_2$ (2×50 ml) and the extract was dried (MgSO$_4$) and concentrated in vacuo to give a yellowish foamy solid. A small portion (100 mg) was subjected to chromatography (SiO$_2$, EtOAc) to give the title compound (68 mg) as a yellow foam. $\delta_H$ (CDCl$_3$) 1.39, 1.41 (6H, s, CMe$_2$), 1.5–1.95 (8H, m, (C$\underline{H}_2$)$_4$), 3.85, 3.88 (3H, s, OMe), 4.11, 4.14 (2H, s, oxazoline C$\underline{H}_2$), 4.55, 4.69 (1H, m, OC$\underline{H}$), 6.6–6.7 (1H, m, ArH), 6.8–6.85 (3H, m, ArH), 6.91 (1H, d, J 6.2 Hz, pyridine $\underline{H}_3$, $\underline{H}_5$), 7.23, 7.38 (2H, d, J 8.2 Hz, ArH), 7.9–8.0 (2H, m, ArH), and 8.3–8.45 (2H, m, pyridine $\underline{H}_2$, $\underline{H}_6$); $\nu_{max}$ (CDCl$_3$) 1735, 1646, 1597 and 1318 cm$^{-1}$; m/z (ESI) 469 (M$^+$, 100%).

EXAMPLE 1

(±)-4-{2-(3-Cyclopentyloxy-4-methoxyphenyl)-2-[4-(4,4-dimethyl-2-oxazolinyl)phenyl]-2-hydroxyethyl}pyridine n-BuLi (1.6M solution in hexanes; 10.3 ml, 16.4 mmol) was added dropwise to 4-methylpyridine (1.45 g, 1.52 ml, 15.6 mmol) in THF (50 ml) at −70° C. After 0.5 h, a solution of intermediate 2 (5.82 g, 14.9 mol) in THF (200 ml) was added via cannula. The reaction was stirred for 2 h at −70° C., allowed to warm to RT then quenched with brine (50 ml). The mixture was extracted with CH$_2$Cl$_2$ (2×50 ml) and the organic layer dried (MgSO$_4$) and concentrated in vacuo to give a gummy yellow solid. Trituration with Et$_2$O gave the title compound (6.61 g) as an off-white solid. $\delta_H$ (CDCl$_3$) 1.37 (6H, s, CMe), 1.55–1.8 (8H, m, (C$\underline{H}_2$)$_4$), 2.7 (1H, br s, O$\underline{H}$), 3.56 (2H, br s, C$\underline{H}_2$ pyridine), 3.82 (3H, s, OMe), 4.10 (2H, s, oxazoline C$\underline{H}_2$), 4.63 (1H, m, OC$\underline{H}$), 6.75–6.9 (5H, m, ArH), 7.37 (2H, d, J 8.6 Hz, pyridine $\underline{H}_3$, $\underline{H}_5$), 7.85 (2H, d, J 7.3 Hz Ar$\underline{H}$ ortho to oxazoline) and 8.29 (2H, br s, pyridine $\underline{H}_2$, $\underline{H}_6$); $\nu_{max}$ (CDCl$_3$) 3603, 1649, 1512, and 1257 cm$^{-1}$; m/z (ESI) 487 (M$^+$+1, 100%), and 394 (61).

EXAMPLE 2

(±)4-{2-(3-Cyclopentyloxy-4-methoxyphenyl)-2-[4-(4,4-dimethyl-2-oxazolinyl)phenyl]ethyl}pyridine A solution of Intermediate 3 (0.27 g, 0.56 mmol) in methanol (15 ml) was treated with ammonium formate (0.70 g, 11.2 mmol) and 10% Pd on carbon (25 mg) and heated to reflux for 6 h. A further portion of ammonium formate (0.70 g, 11.2 mmol) was added and the reaction was heated to reflux for a further 14 h. The reaction was cooled to RT, and the catalyst removed by filtration through a Celite® plug. Concentration of the filtrate under vacuum gave a white foamy solid that was purified by flash column chromatography (eluting with EtOAc) to give the title compound as a clear gum (180 mg). $\delta_H$ (CD$_3$OD) 1.59 (6H, s), Me, 1.62–1.88 (8H,m), 3.75 (3H, s, OMe), 3.78–3.84 (2H, m, C$\underline{H}_2$) 4.64 (1H, t, J 8.2 Hz), 4.77 (2H,m), 6.84 (3H, m), 7.68 (2H, d, J 8.4 Hz), 7.90 (2H, d, J 6.6 Hz), 8.01 (2H, d, J 8.4 Hz), 8.64 (2H, d, J 6.5 Hz). m/z 489 (M$^+$+H$_2$O, 38%), 4.71 (M$^+$, 100), 378 (70), 245 (26).

FORMULATION EXAMPLES

The compounds of the invention may be formulated for pharmaceutical use in a number of forms using any suitable excipients. Thus, for example, for oral use the compounds of the invention such as the compounds of the Examples may be formulated as a solid dosage form, by mixing an appropriate weight of compound (for example 50 mg) with maize starch (50–99% w/w), anhydrous colloidal silica (0–10% w/w) and organic or inorganic acid (up to 1% w/w), to fill capsules of an appropriate size, e.g. white opaque hard gelatine capsules size 3. If desired the same mixture may be compressed into tablets.

The activity and selectivity of compounds according to the invention was demonstrated in the following tests. In these tests the abbreviation FMLP represents the peptide N-formyl-met-leu-phe.

Isolated Enzyme

The potency and selectivity of the compounds of the invention was determined using distinct PDE isoenzymes as follows:
 i. PDE I, rabbit heart
 ii. PDE II, rabbit heart
 iii. PDE ll, rabbit heart, Jurkat cells
 iv. PDE IV, HL60 cells, rabbit brain, rabbit kidney and human recombinant PDE IV
 v. PDE V, rabbit lung, guinea pig lung A gene encoding human PDE IV has been cloned from human monocytes (Livi, et al., 1990, *Molecular and Cellular Biology*, 10, 2678). Using similar procedures we have cloned human PDE IV genes from a number of sources including eosinophils, neutrophils, lymphocytes, monocytes, brain and neuronal tissues. These genes have been transfected into yeast using an inducible vector and various recombinant proteins have been expressed which have the biochemical characteristics of PDE IV (Beavo and Reifsnyder, 1990, TIPS, 11, 150). These recombinant enzymes, particularly the human eosinophil recombinant PDE IV, have been used as the basis of a screen for potent, selective PDE IV inhibitors.

The enzymes were purified to isoenzyme homogeneity using standard chromatographic techniques.

Phosphodiesterase activity was assayed as follows. The reaction was conducted in 150 μl of standard mixture containing (final concentrations): 50 mM 2-[[tris(hydroxymethyl)methyl]amino]-1-ethane-sulphonic acid (TES) —NaOH buffer (pH 7.5), 10 mM MgCl$_2$, 0.1 μM [$^3$H]-cAMP and vehicle or various concentrations of the test compounds. The reaction was initiated by addition of enzyme and conducted at 30° C. for between 5 to 30 mins. The reaction was terminated by addition of 50 μl 2% trifluoroacetic acid containing [$^{14}$C]-5'AMP for determining recovery of the product. An aliquot of the sample was then applied to a column of neutral alumina and the [$^3$H]-cAMP eluted with 10 ml 0.1 TES-NaOH buffer (pH8). The [$^3$H]-5'-AMP product was eluted with 2 ml 2M NaOH into a scintillation vial containing 10 ml of scintillation cocktail. Recovery of [$^3$H]-5'AMP was determined using the [$^{14}$C]-5'AMP and all assays were conducted in the linear range of the reaction.

Compounds according to the invention such as comounds of the Examples herein cause a concentration-dependent inhibition of recombinant PDE IV at 0.1–1000 nM with little or no activity against PDE I, II, III or V at concentrations up to 100 μM.

2. The Elevation of cAMP in Leukocytes

The effect of compounds of the invention on intracellular cAMP was investigated using human neutrophils or guinea pig eosinophils. Human neutrophils were separated from peripheral blood, incubated with dihydrocytochalasin B and the test compound for 10 min and then stimulated with FMLP. Guinea pig eosinophils were harvested by peritoneal lavage of animals previously treated with intraperitoneal injections of human serum. Eosinophils were separated from the peritoneal exudate and incubated with isoprenaline and test compound. With both cell types, suspensions were centrifuged at the end of the incubation, the cell pellets were resuspended in buffer and boiled for 10 min prior to measurement of cAMP by specific radioimmunoassay (DuPont).

The most potent compounds according to the Examples induced a concentration-dependent elevation of cAMP in neutrophils and/or eosinophils at concentrations of 0.1 nM to 1 μM.

3. Suppression of Leukocyte Function

Isolated leukocytes were incubated with dihydrocytochalasin B for superoxide generation only and test compound prior to stimulation with FMLP. The most potent compounds of the Examples caused a concentration-dependent inhibition of superoxide generation, chemotaxis and adhesion at concentrations of 0.1 nM to 1 μM.

Lipopolysaccharide (LPS)-induced synthesis of tumour necrosis factor (TNF) by human peripheral blood monocytes (PBM) is inhibited by compounds of the Examples at concentrations of 0.01 nM to 10 μM.

4. Adverse Effects

In general, in our tests, compounds of the invention have had no observed toxic effects when administered to animals at pharmacologically effective doses.

We claim:
1. A compound of formula (1):

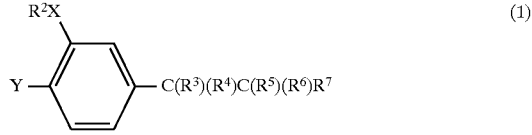

wherein
  Y is a halogen atom or a group —OR$^1$ where R$^1$ is an optionally substituted alkyl group;
  X is —O—, —S— or —N(R$^8$)-, where R$^8$ is a hydrogen atom or an alkyl group;
  R$^2$ is an optionally substituted alkyl, alkenyl, cycloalkyl or cycloalkenyl group;
  R$^3$ is a hydrogen or halogen atom or an —OR$^9$ group, where R$^9$ is a hydrogen atom or an optionally substituted alkyl, alkenyl, alkoxyalkyl or alkanoyl group, or a formyl, carboxamido or thiocarboxamido group;
  R$^4$ is a group —(CH$_2$)$_n$Ar where Ar is a phenyl group which is substituted by an optionally substituted C$_{3-9}$cycloaliphatic group optionally containing one or more heteroatoms selected from oxygen or sulphur atoms or —N($R^8$)- groups, and n is zero or an integer 1, 2 or 3;

$R^5$ is a group —$(CH_2)_n$Ar' where Ar' is a pyridyl group;

$R^6$ is a hydrogen atom or an optionally substituted alkyl group; and $R^7$ is a hydrogen atom or an optionally substituted alkyl group; or a salts, solvate or hydrates thereof.

2. A compound according to claim 1, wherein Y is a group —$OR^1$.

3. A compound according to claim 2, wherein $R^1$ is an optionally substituted straight or branched $C_{1-3}$alkyl group.

4. A compound according to claim 3, wherein $R^1$ is a —$CH_3$ group.

5. A compound according to claim 1 wherein X is —O—.

6. A compound according to claim 1 wherein $R^2$ is a cyclopentyl group.

7. A compound according to claim 1 wherein $R^3$ is a hydrogen atom or a hydroxyl group.

8. A compound according to claim 7, wherein $R^3$ is a hydrogen atom.

9. A compound according to claim 1 wherein $R^6$ and $R^7$ is each a hydrogen atom.

10. A compound according to claim 1, wherein $R^5$ is a 2-, 3- or 4-pyridyl group or a 3,5-disubstituted- or 3-monosubstituted-4-pyridyl group.

11. A compound according to claim 1 wherein $R^4$ is a phenyl group which is substituted by a $C_{3-9}$cycloaliphatic group optionally containing one or more heteroatoms selected from oxygen or sulphur atoms or —N($R^8$)- groups.

12. A compound according to claim 11, wherein Ar is a phenyl group substituted by an optionally substituted cyclobutyl, cyclopentyl, cyclohexyl, 2-cyclopenten-1-yl, pyrrolidinyl, dioxolanyl, imidazolinyl, oxazolinyl, pyranyl, piperidinyl, 1,4-dioxanyl, morpholinyl, thiomorpholinyl or piperazinyl group.

13. A compound which is:
(±)-4-{2-(3-Cyclopentyloxy-4-methoxyphenyl)-2-[4-(4,4-dimethyl-2-oxazolinyl)phenyl]-2-hydroxyethyl}pyridine; or
(±)-4-{2-(3-Cyclopentyloxy-4-methoxyphenyl)-2-[4-(4,4-dimethyl-2-oxazolinyl)phenyl]ethyl}pyridine;
or the resolved enantiomers thereof;
and the salts, solvates, hydrates and N-oxides thereof.

14. A pharmaceutical composition comprising a compound of formula (1):

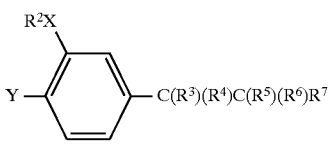

(1)

wherein

Y is a halogen atom or a group —$OR^1$ where $R^1$ is an optionally substituted alkyl group;

X is —O—, —S— or —N($R^8$)-, where $R^8$ is a hydrogen atom or an alkyl group;

$R^2$ is an optionally substituted alkyl, alkenyl, cycloalkyl or cycloalkenyl group;

$R^3$ is a hydrogen or halogen atom or an —$OR^9$ group, where $R^9$ is a hydrogen atom or an optionally substituted alkyl, alkenyl, alkoxyalkyl or alkanoyl group, or a formyl, carboxamido or thiocarboxamido group;

$R^4$ is a group —$(CH_2)_n$Ar where Ar is a phenyl group which is substituted by an optionally substituted $C_{3-9}$cycloaliphatic group optionally containing one or more heteroatoms selected from oxygen or sulphur atoms or —N($R^8$)- groups, and n is zero or an integer 1, 2 or 3;

$R^5$ is a group —$(CH_2)_n$Ar' where Ar' is a pyridyl group;

$R^6$ is a hydrogen atom or an optionally substituted alkyl group; and $R^7$ is a hydrogen atom or an optionally substituted alkyl group;

or a salt, solvate or hydrate thereof;

together with one or more pharmaceutically acceptable carriers, excipients or diluents.

15. A compound according to claim 10 wherein $R^5$ is a 4-pyridyl group.

16. A compound according to claim 12 wherein Ar is a phenyl group substituted by an optionally substituted oxazolinyl group.

17. A compound according to claim 12 wherein said phenyl group is further substituted with one or two substituents selected from the group consisting of halo, methyl, methoxy, trifluoromethyl, hydroxy, formyl and carboxy groups.

18. A compound according to claim 17 wherein said phenyl group is further substituted with one or two methyl groups.

19. A compound according to claim 13 which is (±)-4-{2-(3-Cyclopentyloxy-4-methoxyphenyl)-2-[4-(4,4-dimethyl-2-oxazolinyl)phenyl]-2-hydroxyethyl}-pyridine or a salt, solvate or hydrate thereof.

20. A compound according to claim 13 which is (±)-4-{2-(3-Cyclopentyloxy-4-methoxyphenyl)-2-[4-(4,4-dimethyl-2-oxazolinyl)phenyl]ethyl}pyridine or a salt, solvate or hydrate thereof.

21. A pharmaceutical composition comprising, in combination with one or more pharmaceutically acceptable carriers, excipients or diluents, (±)-4-{2-(3-cyclopentyloxy-4-methoxyphenyl)-2-[4-(4,4-dimethyl-2-oxazolinyl)phenyl]-2-hydroxyethyl}pyridine or (±)-4-{2-(3-cyclopentyloxy-4-methoxyphenyl)-2-[4-(4,4-dimethyl-2-oxazolinyl)phenyl]ethyl}-pyridine or a resolved enantiomer thereof; or a salt, solvate or hydrate thereof.

22. A pharmaceutical composition according to claim 21 which comprises (±)-4-{2-(3-cyclopentyloxy-4-methoxyphenyl)-2-[4-(4,4-dimethyl-2-oxazolinyl)phenyl]-2-hydroxyethyl}pyridine or a resolved enantiomer thereof; or a salt, solvate or hydrate thereof.

23. A pharmaceutical composition according to claim 21 which comprises (±)-4-{2-(3-cyclopentyloxy-4-methoxyphenyl)-2-[4-(4,4-dimethyl-2-oxazolinyl)phenyl]ethyl}-pyridine or a resolved enantiomer thereof; or a salt, solvate or hydrate thereof.

24. A method of preventing or treating an inflammatory disease in a patient comprising administering to said patient a selective inhibitor of a phosphodiesterase (PDE) IV isoenzyme in an amount sufficient to elevate intracellular levels of adenosine 3', 5'-cyclic monophosphate (cAMP), said inhibitor being selected from a compound of formula (1):

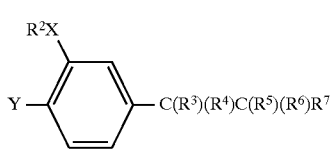

(1)

wherein

Y is a halogen atom or a group —$OR^1$ where $R^1$ is an optionally substituted alkyl group;

X is —O—, —S— or —N(R$^8$)-, where R$^8$ is a hydrogen atom or an alkyl group;

R$^2$ is an optionally substituted alkyl, alkenyl, cycloalkyl or cycloalkenyl group;

R$^3$ is a hydrogen or halogen atom or an —OR$^9$ group, where R$^9$ is a hydrogen atom or an optionally substituted alkyl, alkenyl, alkoxyalkyl or alkanoyl group, or a formyl, carboxamido or thiocarboxamido group;

R$^4$ is a group —(CH$_2$)$_n$Ar where Ar is a phenyl group which is substituted by an optionally substituted C$_{3-9}$cycloaliphatic group optionally containing one or more heteroatoms selected from oxygen or sulphur atoms or —N(R$^8$)- groups, and n is zero or an integer 1, 2 or 3;

R$^5$ is a group —(CH$_2$)$_n$Ar' where Ar' is a pyridyl group;

R$^6$ is a hydrogen atom or an optionally substituted alkyl group; and

R$^7$ is a hydrogen atom or an optionally substituted alkyl group;

or a salt, solvate or hydrate thereof;

together with one or more pharmaceutically acceptable carriers, excipients or diluents.

* * * * *